US008101721B2

(12) United States Patent
Yayon et al.

(10) Patent No.: US 8,101,721 B2
(45) Date of Patent: Jan. 24, 2012

(54) ANTIBODIES BLOCKING FIBROBLAST GROWTH FACTOR RECEPTOR ACTIVATION AND METHODS OF USE THEREOF

(75) Inventors: Avner Yayon, Moshav Sitria (IL); Eran Rom, Rehovot (IL)

(73) Assignee: Fibron Ltd., Ness Ziona (IL)

( * ) Notice: Subject to any disclaimer, the term of this patent is extended or adjusted under 35 U.S.C. 154(b) by 64 days.

(21) Appl. No.: 12/304,638

(22) PCT Filed: Jun. 17, 2007

(86) PCT No.: PCT/IL2007/000732
§ 371 (c)(1),
(2), (4) Date: Aug. 25, 2009

(87) PCT Pub. No.: WO2007/144893
PCT Pub. Date: Dec. 21, 2007

(65) Prior Publication Data
US 2010/0047251 A1    Feb. 25, 2010

Related U.S. Application Data

(60) Provisional application No. 60/813,697, filed on Jun. 15, 2006.

(51) Int. Cl.
*C07K 16/00* (2006.01)
*C12P 21/08* (2006.01)
*A61K 39/395* (2006.01)
*A61K 39/00* (2006.01)

(52) U.S. Cl. ............... 530/387.1; 530/387.3; 424/130.1; 424/133.1; 424/135.1

(58) Field of Classification Search ............... None
See application file for complete search history.

(56) References Cited

U.S. PATENT DOCUMENTS

| | | | |
|---|---|---|---|
| 4,376,110 A | 3/1983 | David et al. | 435/5 |
| 4,816,567 A | 3/1989 | Cabilly | 530/387.3 |
| 4,946,778 A | 8/1990 | Ladner et al. | 435/69.6 |
| 5,091,513 A | 2/1992 | Huston et al. | 530/387 |
| 5,096,815 A | 3/1992 | Ladner et al. | 435/69.1 |
| 5,225,539 A | 7/1993 | Winter | 530/387.3 |
| 5,530,101 A | 6/1996 | Queen et al. | 530/387.3 |
| 5,585,089 A | 12/1996 | Queen et al. | 424/133.1 |
| 5,693,761 A | 12/1997 | Queen et al. | 536/23.53 |
| 5,693,762 A | 12/1997 | Queen et al. | 530/387.3 |
| 5,783,568 A * | 7/1998 | Schlessinger et al. | 514/53 |
| 5,910,573 A | 6/1999 | Plückthun et al. | 530/387.3 |
| 6,300,064 B1 | 10/2001 | Knappik | 435/6 |
| 6,342,221 B1 * | 1/2002 | Thorpe et al. | 424/178.1 |
| 6,608,181 B2 | 8/2003 | Lorenzi et al. | 530/387.9 |
| 6,683,082 B2 | 1/2004 | Tang et al. | 514/249 |
| 6,900,053 B2 | 5/2005 | Freier | 435/375 |
| 6,987,113 B2 | 1/2006 | Tang et al. | 514/265.1 |
| 2003/0044521 A1 | 3/2003 | Gan et al. | 427/96 |
| 2009/0263836 A1 * | 10/2009 | Fernandez-Salas et al. | 435/7.32 |

FOREIGN PATENT DOCUMENTS

| | | |
|---|---|---|
| EP | 173 494 | 3/1986 |
| EP | 184 187 | 6/1986 |
| EP | 125 023 | 6/1991 |
| EP | 171 496 | 5/1993 |
| WO | WO 86/01533 | 3/1986 |
| WO | WO 90/07861 | 7/1990 |
| WO | WO 92/22653 | 12/1992 |
| WO | WO 93/15210 | 8/1993 |
| WO | WO 96/13583 | 5/1996 |
| WO | WO 96/37621 | 11/1996 |
| WO | WO 97/02671 | 1/1997 |
| WO | WO 97/08320 A1 | 3/1997 |
| WO | WO 02/102972 A2 | 12/2002 |
| WO | WO 03/023004 A2 | 3/2003 |
| WO | WO 03/024987 A1 | 3/2003 |
| WO | WO 2004/110487 A1 | 12/2004 |
| WO | WO 2005/066211 A2 | 7/2005 |
| WO | WO 2006/048877 A2 | 5/2006 |

OTHER PUBLICATIONS

Skolnick and Fetrow. From genes to protein structure and function: novel applications of computational approaches in the genomic era. Trends in Biotechnology, 2000. vol. 18, pp. 34-39.*
Mac Callum, Martin, and Thornton. Antibody-antigen interactions: contact analysis and binding site topography. Journal of Molecular Biology, 1996. vol. 262, pp. 732-745.*
Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*
Vajdos, Adams, Breece, Presta, De Vos, and Sidhu. Comprehensive functional maps of the antigen-binding site of an anti-ErbB2 antibody obtained with shotgun scanning mutagenesis. Journal of Molecular Biology, 2002. vol. 320, pp. 415-428.*
Wu, Nie, Huse, and Watkins. Humanization of a murine monoclonal antibody by simultaneous optimization of framework and CDR residues. Journal of Molecular Biology, 1999. vol. 294, pp. 151-162.*
Rudikoff, Giusti, Cook, and Scharff. Single amino acid substitution altering antigen-binding specificity. Proceedings of the National Academy of Sciences, 1982. vol. 79, pp. 1979-1982.*
De Pascalis, Iwahashi, Tamura, Padlan, Gonzales, Santos, Giuliano, Schuck, Schlom, and Kashmiri. Grafting of abbreviated complementarity-determining regions containing specificity determining residues essential for ligand contact to engineer a less immunogenic humanized monoclonal antibody. Journal of Immunology, 2002. vol. 169, pp. 3076-3084.*
Holm, Jafari, and Sundstrom. Functional mapping and single chain construction of the anti-cytokeratin 8 monoclonal antibody TS1. Molecular Immunology, 2007. vol. 44, pp. 1075-1084.*
Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*
International Search Report PCT/IL07/000732 Dated Aug. 13, 2008.
Bange et al., 2002 Cancer Research 62(3):840-847.

(Continued)

*Primary Examiner* — Anne M. Gussow
(74) *Attorney, Agent, or Firm* — Winston & Strawn LLP

(57) ABSTRACT

The present invention is related to antibodies with binding affinity to fibroblast growth factor receptor 2 (FGFR2) optionally with binding affinity to other FGF receptors, which block both ligand-dependent and constitutive ligand independent receptor activation. Specifically, the present invention relates to antibodies with high affinity to more than one FGF receptor subtype, and fragments thereof, useful in treating disorders including cell proliferative diseases.

16 Claims, 11 Drawing Sheets

OTHER PUBLICATIONS

Bernard-Pierrot et al., 2004 Oncogene 23(57):9201-9211.
Better et al., 1988 Science 240(4855):1041-1043.
Billerey et al., 2001 Am. J. Pathol. 158(6):1955-1959.
Cabilly et al., 1984 Proc. Natl. Acad. Sci. USA 81(11):3273-3277.
Cappellen et al., 1999 Nature Genetics 23(1):18-20.
Easton et al., 2007 Nature 447(7148):1087-1093.
Fortin et al., 2005 J. Neurosci. 25(32):7470-7479.
Grigoriadis et al., 1988 J. Biol. Chem. 263(22):10927-10931.
Hunter et al., 2007 Nature Genetics 39(6):870-874.
Ishiwata et al., 1998 Am. J. Pathol. 153(1):213-222.
Johnston et al., 1995 J. Biol. Chem. 270(51):30643-30650.
Kan et al., 1993 Science 259(5103):1918-1921.
Khnykin et al., 2006 J. Pathol. 208(3):431-438.
Knappik et al., 2000 J. Mol. Biol. 296(1):57-86.
Kohler et al., 1975 Nature 256:495-497.
Kubota et al., 2000 Developmental Dynamics 217(2):170-179.
Kurban et al., 2004 Oncology Report 11(5):987-991.
Larocca et al., 1998 Hybridoma 17(1):21-31.
Lorenzi et al., 1996 Proc. Natl. Acad. Sci. USA. 93(17):8956-8961.
Low, 2002 J. Clin. Invest. 109(1):15-16.
Martinez-Torrecuadrada et al., 2005 Clinical Cancer Research 11:6280-6290.
Meinkoth et al., 1984 Anal. Biochem. 138(2):267-284.
Muller et al., 1998 FEBS Lett. 432(1):45-49.
Ornitz et al., 2001 Genome Biology 2(3):reviews3005.1-3005.12.
Ricol et al., 1999 Oncogene 18(51):7234-7243.
Saltzman et al., 1989 Biophys. J. 55(1):163-171.
Sherwood et al., 1992 Nature Biotechnology 10(11):1446-1449.
van Rhijn et al., 2002 Eur J Hum Genet 10(12):819-824.
Yee et al., 2000 J. Natl. Cancer Inst. 92(22):1848-1849.
Zhang et al., 2000 Biopolymers 54(6):464-475.
Zieger et al., 2005 Clinical Cancer Research 11(21):7709-7719.
International Preliminary Report on Patentability PCT/IL07/00732 dated Mar. 17, 2009.
Supplementary European Search Report EP 07766788 Dated Oct. 5, 2009.
Köhler et al., "Different Was to Modify Monoclonal Antibodies," Med. Oncol. & Tumor Pharmacother. 1(4):227-223 (1984).
Müller et al., "The first constant domain ($C_H1$ and $C_L$) of an antibody used as heterodimerization domain for bispecific miniantibodies," FEBS Letters 422:259-264 (1998).

* cited by examiner

Figure 6C      Figure 6D

SEQUENCE LISTING

<160> NUMBER OF SEQ ID NOS: 14

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ser Tyr Tyr Pro Asp Phe Asp Tyr
1               5

<210> SEQ ID NO 2
<211> LENGTH: 10
<212> TYPE: PRT
<213> ORGANISM: Artificial Sequence
<220> FEATURE:
<223> OTHER INFORMATION: Synthetic peptide

<400> SEQUENCE: 2

Gln Ser Tyr Ala Ser Gln Gly Ile His Tyr
1               5                   10

<210> SEQ ID NO 3
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 3
tcttattatc ctgattttga ttat                                              24

<210> SEQ ID NO 4
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 4
cagtcttatg cttctcaggg tattcattat                                        30

<210> SEQ ID NO 5
<211> LENGTH: 250
<212> TYPE: PRT
<213> ORGANISM: Artificial Sequence
<220> FEATURE:
<223> OTHER INFORMATION: Synthetic peptide

<400> SEQUENCE: 5

Met Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Gly Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val

```
                    85                  90                  95
Tyr Tyr Cys Ala Arg Ser Tyr Tyr Pro Asp Phe Asp Tyr Trp Gly Gln
            100                 105                 110

Gly Thr Leu Val Thr Val Ser Ser Ala Gly Gly Gly Ser Gly Gly Gly
        115                 120                 125

Gly Ser Gly Gly Gly Ser Gly Gly Gly Ser Asp Ile Glu Leu
    130                 135                 140

Thr Gln Pro Pro Ser Val Ser Val Ala Pro Gly Gln Thr Ala Arg Ile
145                 150                 155                 160

Ser Cys Ser Gly Asp Ala Leu Gly Asp Lys Tyr Ala Ser Trp Tyr Gln
                165                 170                 175

Gln Lys Pro Gly Gln Ala Pro Val Leu Val Ile Tyr Asp Asp Ser Asp
            180                 185                 190

Arg Pro Ser Gly Ile Pro Glu Arg Phe Ser Gly Ser Asn Ser Gly Asn
        195                 200                 205

Thr Ala Thr Leu Thr Ile Ser Gly Thr Gln Ala Glu Asp Glu Ala Asp
    210                 215                 220

Tyr Tyr Cys Gln Ser Tyr Ala Ser Gln Gly Ile His Tyr Val Phe Gly
225                 230                 235                 240

Gly Gly Thr Lys Leu Thr Val Leu Gly Gln
                245                 250

<210> SEQ ID NO 6
<211> LENGTH: 753
<212> TYPE: DNA
<213> ORGANISM: Artificial Sequence
<220> FEATURE:
<223> OTHER INFORMATION: Synthetic oligonucleotide

<400> SEQUENCE: 6
atggtgcaat tgcaacagtc tggtccgggc ctggtgaaac cgagccaaac cctgagcctg      60
acctgtgcga tttccggaga tagcgtgagc agcaacagcg cggcgtggaa ctggattcgc     120
cagtctcctg gcgtggcct cgagtggctg gccgtacct attatcgtag caaatggtat       180
aacgattatg cggtgagcgt gaaaagccgg attaccatca cccggatac ttcgaaaaac      240 cagtttagcc tgcaactgaa cagcgtgacc ccggaagata cggccgtgta ttattgcgcg     300
cgttcttatt atcctgattt tgattattgg ggccaaggca ccctggtgac ggttagctca     360
gcgggtggcg gttctggcgg cggtgggagc ggtggcggtg gttctggcgg tggtggttcc     420
gatatcgaac tgacccagcc gccttcagtg agcgttgcac aggtcagac cgcgcgtatc      480 tcgtgtagcg gcgatgcgct gggcgataaa tacgcgagct ggtaccagca gaaacccggg     540
caggcgccag ttctggtgat ttatgatgat tctgaccgtc cctcaggcat cccggaacgc     600
tttagcggat ccaacagcgg caacaccgcg accctgacca ttagcggcac tcaggcggaa     660
gacgaagcgg attattattg ccagtcttat gcttctcagg gtattcatta tgtgtttggc     720
ggcggcacga agttaaccgt tcttggccag tga                                  753

<210> SEQ ID NO 7
<211> LENGTH: 249
<212> TYPE: PRT
<213> ORGANISM: Artificial Sequence
<220> FEATURE:
<223> OTHER INFORMATION: Synthetic peptide

<400> SEQUENCE: 7

Met Val Gln Leu Gln Gln Ser Gly Pro Gly Leu Val Lys Pro Ser Gln
1               5                   10                  15
```

-continued

```
Thr Leu Ser Leu Thr Cys Ala Ile Ser Gly Asp Ser Val Ser Ser Asn
             20                  25                  30

Ser Ala Ala Trp Asn Trp Ile Arg Gln Ser Pro Gly Arg Gly Leu Glu
         35                  40                  45

Trp Leu Gly Arg Thr Tyr Tyr Arg Ser Lys Trp Tyr Asn Asp Tyr Ala
 50                  55                  60

Val Ser Val Lys Ser Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Tyr Tyr Cys Ala Arg Ser Tyr Tyr Pro Asp Phe Asp Tyr Trp Gly Gln
            100                 105                 110

Gly Thr Leu Val Thr Val Ser Ser Ala Gly Gly Ser Gly Gly Gly
            115                 120                 125

Gly Ser Gly Gly Gly Ser Gly Gly Gly Ser Asp Ile Glu Leu
        130                 135                 140

Thr Gln Pro Pro Ser Val Ser Val Ala Pro Gly Gln Thr Ala Arg Ile
145                 150                 155                 160

Ser Cys Ser Gly Asp Ala Leu Gly Asp Lys Tyr Ala Ser Trp Tyr Gln
            165                 170                 175

Gln Lys Pro Gly Gln Ala Pro Val Leu Val Ile Tyr Asp Asp Ser Asp
            180                 185                 190

Arg Pro Ser Gly Ile Pro Glu Arg Phe Ser Gly Ser Asn Ser Gly Asn
            195                 200                 205

Thr Ala Thr Leu Thr Ile Ser Gly Thr Gln Ala Glu Asp Glu Ala Asp
        210                 215                 220

Tyr Tyr Cys Gln Ser Tyr Asp Gly Pro Asp Leu Trp Val Phe Gly Gly
225                 230                 235                 240

Gly Thr Lys Leu Thr Val Leu Gly Gln
            245
```

<210> SEQ ID NO 8
<211> LENGTH: 750
<212> TYPE: DNA
<213> ORGANISM: Artificial Sequence
<220> FEATURE:
<223> OTHER INFORMATION: Synthetic oligonucleotide

<400> SEQUENCE: 8

| | | |
|---|---|---|
| atggtgcaat tgcaacagtc tggtccgggc ctggtgaaac cgagccaaac cctgagcctg | 60 |
| acctgtgcga tttccggaga tagcgtgagc agcaacagcg cggcgtggaa ctggattcgc | 120 |
| cagtctcctg gcgtggcct cgagtggctg ggccgtacct attatcgtag caaatggtat | 180 |
| aacgattatg cggtgagcgt gaaaagccgg attaccatca cccggatac ttcgaaaaac | 240 |
| cagtttagcc tgcaactgaa cagcgtgacc ccggaagata cggccgtgta ttattgcgcg | 300 |
| cgttcttatt atcctgattt tgattattgg ggccaaggca ccctggtgac ggttagctca | 360 |
| gcgggtggcg gttctggcgg cggtgggagc ggtggcggtg gttctggcgg tggtggttcc | 420 |
| gatatcgaac tgacccagcc gccttcagtg agcgttgcac aggtcagac cgcgcgtatc | 480 |
| tcgtgtagcg gcgatgcgct gggcgataaa tacgcgagct ggtaccagca gaaacccggg | 540 |
| caggcgccag ttctggtgat ttatgatgat tctgaccgtc cctcaggcat cccggaacgc | 600 |
| tttagcggat ccaacagcgg caacaccgcg accctgacca ttagcggcac tcaggcggaa | 660 |
| gacgaagcgg attattattg ccagagctat gacggtcctg atctttgggt gtttggcggc | 720 |

```
ggcacgaagt taaccgttct tggccagtga                                    750
```

<210> SEQ ID NO 9
<211> LENGTH: 17
<212> TYPE: PRT
<213> ORGANISM: Artificial Sequence
<220> FEATURE:
<223> OTHER INFORMATION: Synthetic peptide

<400> SEQUENCE: 9

Asn Met Ala Tyr Thr Asn Tyr Gln Tyr Val Asn Met Pro His Phe Asp
1               5                   10                  15

Tyr

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

Gln Ser Tyr Asp Tyr Phe Lys Leu
1               5

<210> SEQ ID NO 11
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 11

```
aatatggctt atactaatta tcagtatgtt aatatgcctc attttgatta t            51
```

<210> SEQ ID NO 12
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 12

```
cagagctatg actattttaa gctt                                          24
```

<210> SEQ ID NO 13
<211> LENGTH: 107
<212> TYPE: PRT
<213> ORGANISM: Artificial Sequence
<220> FEATURE:
<223> OTHER INFORMATION: Synthetic peptide

<400> SEQUENCE: 13

Val Gln Leu Gln Gln Ser Gly Pro Gly Leu Val Lys Pro Ser Gln Thr
1               5                   10                  15

Leu Ser Leu Thr Cys Ala Ile Ser Gly Asp Ser Val Ser Ser Asn Ser
                20                  25                  30

Ala Ala Trp Ser Trp Ile Arg Gln Ser Pro Gly Arg Gly Leu Glu Trp
            35                  40                  45

Leu Gly Arg Thr Tyr Tyr Arg Ser Lys Trp Tyr Asn Asp Tyr Ala Val
        50                  55                  60

Ser Val Lys Ser Arg Ile Thr Ile Asn Pro Asp Thr Ser Lys Asn Gln
65                  70                  75                  80

Phe Ser Leu Gln Leu Asn Gly Val Thr Pro Glu Asp Thr Ala Val Tyr

```
                    85                  90                  95
Tyr Cys Ala Arg Ser Tyr Tyr Pro Asp Phe Asp
                100                 105

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide

<400> SEQUENCE: 14

Ser Tyr Tyr Pro Asp Phe Asp
1               5
```

ANTIBODIES BLOCKING FIBROBLAST GROWTH FACTOR RECEPTOR ACTIVATION AND METHODS OF USE THEREOF

This application is a 371 filing of International Patent Application PCT/IL2007/000732 filed Jun. 17, 2007, which claims the benefit of application no. 60/813,697 filed Jun. 15, 2006.

FIELD OF THE INVENTION

The present invention is related in general to antibodies with binding affinity to fibroblast growth factor receptors (FGFRs) which block both ligand-dependent and constitutive ligand independent receptor activation. In particular, the present invention relates to antibodies specific for more than one receptor subtype, and fragments thereof, useful for treating diseases and disorders, including cell proliferative diseases.

BACKGROUND OF THE INVENTION

Fibroblast Growth Factor Receptors

Fibroblast Growth Factor ligands (FGFs) constitute a family of over twenty structurally related polypeptides that are developmentally regulated and expressed in a wide variety of tissues. FGFs stimulate proliferation, cell migration and differentiation and play a major role in skeletal and limb development, wound healing, tissue repair, hematopoiesis, angiogenesis, and tumorigenesis (reviewed in Ornitz and Itoh, 2001).

The biological action of FGFs is mediated by specific cell surface receptors belonging to the receptor protein tyrosine kinase (RPTK) family of protein kinases. These proteins consist of an extracellular ligand binding domain, a single transmembrane domain and an intracellular tyrosine kinase domain that undergoes phosphorylation upon binding of FGF. The FGF receptor (FGFR) extracellular region contains three immunoglobulin-like (Ig-like) domains (D1, D2 and D3), an acidic box, and a heparin-binding domain. Five FGFR genes encoding for multiple receptor variants have been identified to date. Alternative splicing further increases the diversity of the FGFR family. The second half of the third Ig-like domain in FGFR1, 2 and 3 is encoded by one of two exons, IIIb or IIIc, generating receptors with different ligand affinities and specificities.

Fibroblast Growth Factor Receptors and Malignancy

Certain FGFRs have been implicated in certain malignancies and proliferative diseases. FGFR3 is the most frequently mutated oncogene in transitional cell carcinoma (TCC) of the bladder where it is mutated in more than 30% of the cases (Cappellen 1999). Yee et al. (2000) identified a mutation in FGFR3 linked to cervical carcinoma. van Rhijn et al. (2002) disclosed FGFR3 mutations in bladder cancer which were previously identified in skeletal disorders.

FGFR3 mutations seem to have a central role in the early development of papillary bladder tumors and can serve as a target for treatment (Billerey et al., 2001; Cappellen et al., 1999). These tumors follow a common molecular pathway, which is different from tumors with concomitant carcinoma in situ (CIS). However, FGFR3 mutations do not seem to play a role in bladder cancer progression (Zieger, et al., 2005).

FGFR2 mRNAs were found to be overexpressed in both human pancreatic cancer cells and the adjacent pancreatic parenchyma (Ishiwata et al., 1998,) and Kurban et al., (2004) identified FGFR IIIb (KGFR) expression in cervical cancer cells. Lorenzi et al. (1996) have identifies a constitutively active form of FGFR2 in rat osteosarcoma cells.

In general, FGFR2 exhibits expression of the IIIb isoform in epithelial type tissues and the uroepithelium and the IIIc isoform in the mesenchyme. FGFR2 subtype IIIb (FGFR2-IIIb) was shown to have tumor suppressive properties, i.e. be downregulated in a subset of transitional cell carcinomas of the bladder (Bernard-Pierrot et al., 2004; Ricol et al. 1999).

Johnston et al. (1995) reported that FGFR4 and FGFR2 are expressed at higher levels in breast cancer cell lines than in normal epithelial cells. Khnykin D et al. (2006) found that in the majority of cases FGF2-FGFR4, but not FGFR1, were expressed by malignant cells. FGFR4 was shown to be associated with pituitary tumors (Ezzat, et al, 2002) and breast cancer progression (Bange, et al., 2002).

Recent findings implicate that single nucleotide polymorphisms (SNPs) in FGFR2 were highly associated with breast cancer (Hunter et al., 2007). An additional study demonstrated that SNPs in five novel independent loci including FGFR2 exhibited strong and consistent evidence of association with breast cancer (Easton et al., 2007).

These and other findings implicate the involvement of both FGFR2 and FGFR3 in the pathogenesis of various malignancies rendering these FGF receptors potential targets for therapeutic intervention in these cell proliferative diseases.

Fibroblast Growth Factor Receptor Inhibitors

International Patent Publication WO 03/024987 discloses antisense compounds useful for modulating FGFR2. International Patent Publication WO 03/023004 discloses antisense compounds useful for modulating FGFR3. U.S. Pat. No. 6,900,053 teaches compositions comprising antisense oligonucleotides and methods for modulating the expression of FGFR2. Those compositions were found useful in the treatment of diseases associated with overexpression of FGFR2. Small molecule tyrosine kinase inhibitors, which have been shown to inhibit the activity of certain tyrosine kinase receptors, are disclosed in U.S. Pat. Nos. 6,987,113; 6,683,082 and others.

International Patent Publication WO 02/102972, co-assigned to the assignee of the present invention and incorporated by reference herein, discloses antibodies to receptor protein tyrosine kinases, specifically anti-fibroblast growth factor receptor 3 (FGFR3) antibodies. Certain antibodies shown to be specific for FGFR3 neutralize FGFR3 activity and are potentially useful for treating skeletal dysplasias such as achondroplasia and proliferative diseases such as multiple myeloma. That disclosure notes bladder cancer in a list of proliferative diseases in which FGFR3 is known to be involved but does not teach the method of treating or attenuating bladder cancer using an anti-FGFR2 antibody.

PCT Publication WO 2006/048877, co-assigned to the assignee of the present invention teaches a method of treating multiple myeloma comprising administering to an individual in need thereof an anti-FGFR3 antibody which is specific for wild type FGFR3.

PCT Publication WO 2004/110487 assigned to the assignee of the present invention, provides a method of treating a T cell mediated disease comprising administering to a subject in need thereof an FGFR3 antagonist.

International Patent Publication WO 2005/066211 teaches antibodies directed to FGFR polypeptides, and methods of use thereof for treating tumors. That application provides tables disclosing human tumors, which express the various FGFR proteins but there is no teaching of cross reactive antibodies. Martínez-Torrecuadrada et al. (2005) teach anti-FGFR3 antibodies which inhibit bladder carcinoma cell proliferation.

Kan et al. (1993) disclose that heparin interacts with a specific region in the extracellular domain of the FGFR, and is essential for FGFR activation. They synthesized a peptide corresponding to the heparin binding domain of FGFR1 and raised polyclonal antibodies specific to this peptide. Both the peptide and the antibodies were antagonistic to FGF1-stimulated cell growth. However, Kan et al. did not demonstrate blocking of other FGF receptors nor do they show inhibition of constitutive receptor activation.

Fortin et al. (2005) used antibodies specific to a single receptor subtype, namely either FGFR1, FGFR2 or FGFR3 to examine FGF/FGFR interactions during oligodendrocyte development. In this article there is no teaching of an antibody that binds both FGFR2 and FGFR3 with high affinity.

Nowhere in the art is it suggested that anti-FGFR antibodies cross-reactive with more than one receptor subtype would be particularly useful for treating neoplasms. Nowhere in the prior art was it taught or suggested that antibodies capable of blocking heparin binding to the heparin binding site of an FGF receptor could exhibit cross-reactivity to multiple receptor subtypes. Thus, there is an unmet need for anti-FGFR antibodies capable of blocking both ligand-dependent and aberrant constitutive ligand-independent FGF receptor activation, thereby modulating various biological abnormalities.

SUMMARY OF THE INVENTION

The present invention provides antibodies having high specificity to fibroblast growth factors of more than one subtype. The present invention further provides antibodies having high affinity to fibroblast growth factor receptor 2 (FGFR2) having cross-reactivity to other fibroblast growth factor receptors (FGFRs) useful in blocking both ligand-dependent and constitutive ligand-independent receptor activation. It is now disclosed that antibodies cross-reactive to FGFR2 and/or FGFR3 are useful in the prevention, attenuation or treatment of cell proliferative diseases of epithelial origin including but not limited to bladder cancer, breast cancer, ovarian cancer, prostate cancer, osteosarcoma and chondrosarcoma. Without wishing to be bound by any particular theory or mechanism of action, these antibodies may block receptor activation by blocking either FGF binding or heparin binding or both.

In one aspect the present invention is related to molecules comprising at least the antigen-binding portion of an antibody having affinity for fibroblast growth factor receptor 2 (FGFR2) optionally with cross-reactivity to other FGF receptors, which block both ligand-dependent and constitutive ligand-independent receptor activation.

According to certain embodiments of the present invention, the antibody which blocks activation of fibroblast growth factor receptors (FGFR) has high affinity to both FGFR2 and FGFR3. According to particular embodiments the antibody has affinity of at least 50 nM (KD<50 nM), to both FGFR2 and FGFR3. Preferably the antibody of the invention has an affinity of at least 10 nM to both FGFR2 and FGFR3. According to some embodiments the antibody is substantially devoid of affinity to FGFR1.

According to some embodiments of the present invention, the antibody having affinity for FGFR2 with cross-reactivity to other FGF receptors is selected from a monoclonal antibody, and a fragment of a monoclonal antibody including but not limited to Fab, F(ab')$_2$ and single chain Fv (scFv). Additional embodiments include chimeric antibodies; human and humanized antibodies; recombinant and engineered antibodies, and fragments thereof. A preferred antibody species is a single chain antibody. Single chain antibodies can be single chain composite polypeptides having antigen binding capabilities and comprising amino acid sequences homologous or analogous to the variable regions of an immunoglobulin light and heavy chain i.e. linked $V_H$-$V_L$ or single chain Fv (scFv).

In one embodiment, the molecule comprising at least the antigen-binding portion of an antibody having affinity for FGFR2 with cross-reactivity to other FGF receptors, consists of a $V_H$-CDR3 region and a $V_L$-CDR3 region having SEQ ID NO:1 and SEQ ID NO:2, respectively. In another embodiment the molecule comprising at least the antigen-binding portion of an antibody having affinity for FGFR2 with cross-reactivity to other FGF receptors, is a single chain Fv molecule (ScFv) having SEQ ID NO:5, having corresponding polynucleotide sequence SEQ ID NO:6.

According to some embodiments of the present invention the fragment of the antibody having affinity for FGFR2 with cross-reactivity to other FGF receptors is modified. According to other embodiments the modification is PEGylation.

In another aspect the present invention is related to a pharmaceutical composition useful for preventing, attenuating or treating a disease or disorder associated with FGFR comprising a therapeutically effective amount of a molecule comprising at least the antigen-binding portion of an antibody having affinity for FGFR2 with cross-reactivity to other FGF receptors; and a pharmaceutically acceptable carrier.

According to certain embodiments the disease or disorder associated with FGFR2 is a cell proliferative disease or disorder. According to other embodiments the cell proliferative disease or disorder is of epithelial origin. According to additional embodiments cell proliferative diseases or disorders include but are not limited to bladder cancer, breast cancer, ovarian cancer, prostate cancer, osteosarcoma and chondrosarcoma.

In yet another aspect the present invention is related to a method of preventing, attenuating or treating a disease or disorder associated with FGFR2, comprising administering to a subject in need thereof a pharmaceutical composition comprising a therapeutically effective amount of an antibody having affinity to FGFR2 with cross-reactivity to other FGF receptors; and a pharmaceutically acceptable carrier. According to some embodiments the disease or disorder associated with FGFR2 is a cell proliferative disease or disorder of epithelial origin selected from bladder cancer, breast cancer, ovarian cancer, prostate cancer, osteosarcoma and chondrosarcoma.

Another aspect of the present invention relates to the use of a molecule comprising at least the antigen-binding portion of an antibody having affinity for FGFR2 optionally with cross-reactivity to other FGF receptors, for the manufacture of a therapeutic composition for the treatment of a cell proliferative disease or disorder including but not limited to bladder cancer, breast cancer, ovarian cancer, prostate cancer, osteosarcoma and chondrosarcoma.

Yet another aspect of the present invention is related to the use of a pharmaceutical composition comprising at least the antigen-binding portion of an antibody having affinity for FGFR2 with cross-reactivity to other FGF receptors for the treatment of a cell proliferative disease or disorder, wherein the cell proliferative disease or disorder is selected from bladder cancer, breast cancer, ovarian cancer, prostate cancer, osteosarcoma and chondrosarcoma.

It is to be understood that treatment of a cell proliferative disease includes treatment of a primary tumor as well as prevention or treatment of metastases.

The FGFR according to the present invention is preferably human, however other mammalian FGFR proteins are within the scope of the invention. These and other aspects of the present invention will be apparent from the figures, description, and claims that follow.

DETAILED DESCRIPTION OF THE INVENTION

Figure 1A:
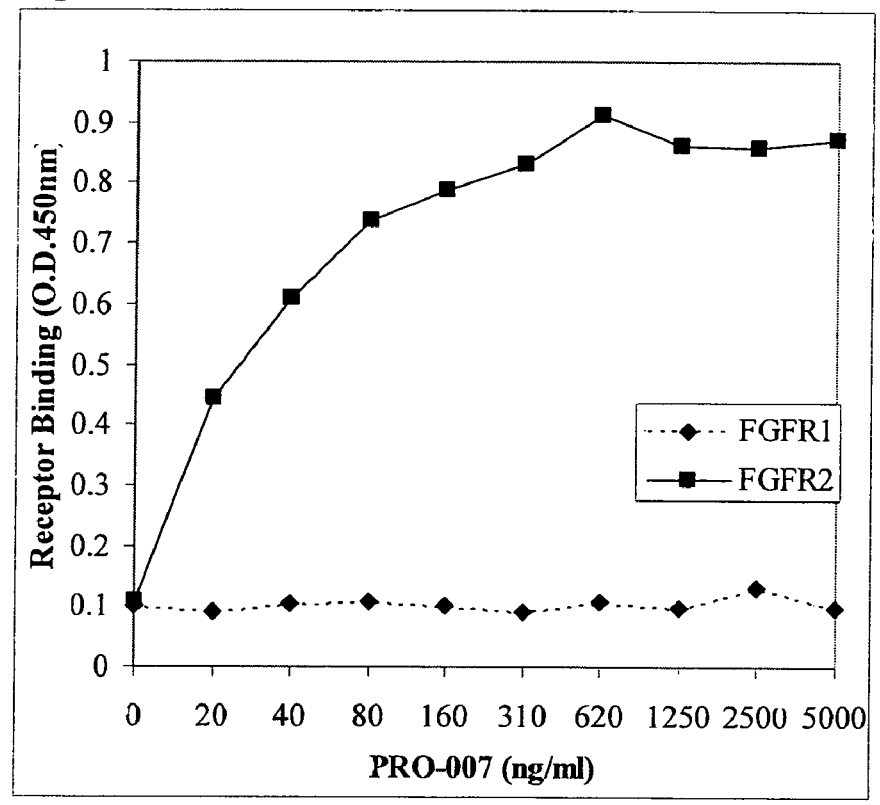
FIG. 1. Binding specificity of three antibodies to FGF receptors. A) PRO-007 binds FGFR2 with high affinity; B) Both PRO-007 and PRO-001 bind FGFR3 with high affinity; C) PRO-001 binds FGFR3 with high affinity but FGFR3 with low affinity; D) PRO-008 binds both FGFR1 and FGFR3 with high affinity.

The present invention provides for the first time antibodies with high affinity to fibroblast growth factor receptor 2 (FGFR2) optionally having cross-reactivity to other fibroblast growth factor receptors (FGFRs); and fragments thereof, which are efficient in blocking both ligand-dependent and constitutive ligand-independent receptor activation. These antibodies were found highly effective in blocking cell proliferation of abnormal cell types including bladder cancer and osteosarcoma cell lines.

Various indications support the notion that more than one FGF receptor subtype may be involved in the pathogenesis of many cell proliferative diseases. Without wishing to be bound by theory, cross-reactivity of the antibodies to more than one FGFR subtype may be advantageous for clinical treatment.

According to one aspect the present invention is related to a composition comprising at least the antigen-binding portion of an antibody which has affinity for FGFR2 optionally with cross-reactivity to other FGF receptors, which blocks both ligand-dependent and constitutive ligand-independent receptor activation. According to another aspect the present invention involves a pharmaceutical composition for the prevention, attenuation or treatment of a disease or disorder associated with FGFR2, comprising at least the antigen-binding portion of an antibody which has affinity for FGFR2 with cross-reactivity to other FGF receptors; and a pharmaceutically acceptable carrier.

In one aspect the present invention relates to a method for the prevention, attenuation or treatment of cell proliferative diseases comprising administering to a subject in need thereof a therapeutically effective amount of a molecule comprising the antigen-binding portion of an antibody having affinity for FGFR2 with cross-reactivity to other FGF receptors; and a pharmaceutically acceptable carrier. In a non-limiting example, the present invention relates to a method for the prevention, attenuation or treatment of bladder cancer comprising administering to a subject in need thereof a therapeutically effective amount of a molecule comprising the antigen-binding portion of an isolated antibody having affinity for FGFR2 and/or FGFR3; and a pharmaceutically acceptable carrier.

Another aspect relates to the use of a molecule comprising the antigen-binding portion of an isolated antibody having affinity for FGFR2 with cross-reactivity to other FGF receptors, for the manufacture of a therapeutic composition for the treatment of cell proliferative diseases. Yet another aspect concerns the use of a pharmaceutical composition comprising at least the antigen-binding portion of an antibody which has affinity for FGFR2 with cross-reactivity to other FGF receptors, for the treatment of a cell proliferative disease or disorder including but not limited to bladder cancer, breast cancer, ovarian cancer, prostate cancer, osteosarcoma and chondrosarcoma.

According to certain embodiments, the antibody, which blocks both ligand-dependent and constitutive (ligand-independent) receptor activation, has binding affinity of at least 50 nM to both FGFR2 and FGFR3. Preferably the antibody will have affinity of at least 10 nM for both FGFR2 and FGFR3. According to other embodiments, the antigen-binding portion of an isolated antibody having affinity for FGFR2 and/or FGFR3 is selected from monoclonal antibodies, a monoclonal antibody fragment or an antibody-fusion protein. The affinity of a given antibody to various receptor subtypes can be easily measured using methods known to one of skill in the art. By way of example, antibody affinities to receptor subtypes may conveniently be measured using the BIACORE® technology (AB Corporation, Sweden), among others. Using this technology, antibodies of the present invention were found to have affinities of less than 10 nM to both FGFR2 and FGFR3, whereas affinities to FGFR1 were undetectable using this method.

According to one embodiment the antibody of the invention binds to the heparin binding site of at least one or more subtype of FGF receptor. According to another embodiment the antibody of the invention prevents heparin from binding to the heparin binding site of the FGFRs. According to yet another embodiment the antibody of the invention blocks both ligand-dependent and constitutive ligand-independent receptor activation. According to some embodiments the antibody binds to the heparin binding site of a plurality of FGFR subtypes.

PCT publication WO 02/102972, co-assigned to some of the assignees of the present invention, discloses monoclonal antibodies to receptor protein tyrosine kinases, including specific anti-Fibroblast Growth Factor Receptor antibodies, the contents of which are incorporated in their entirety. A soluble dimeric form of the extracellular domain of the FGFR3 receptor was utilized to screen for antibodies (e.g., Fabs) from a phage display antibody library. This screening yielded numerous high affinity antibodies (Fabs, $K_D$<50 nM) that bind FGFR3 and interfere with ligand binding, thereby blocking ligand-dependent activation of FGFR3. Certain antibodies were shown to be specific for FGFR3 and useful to neutralize FGFR3 activity and for the treatment of skeletal dysplasias such as achondroplasia and proliferative diseases such as bladder cancer and multiple myeloma.

Definitions

For convenience certain terms employed in the specification, examples and claims are described herein.

Fibroblast Growth Factor Receptors

The term "fibroblast growth factor receptor" or "FGFR" denotes a receptor specific for FGF which is necessary for transducing the signal exerted by FGF to the cell interior, typically comprising an extracellular ligand-binding domain, a single transmembrane helix, and a cytoplasmic domain having tyrosine kinase activity. The FGFR extracellular domain consists of three immunoglobulin-like (Ig-like) domains (D1, D2 and D3), a heparin binding domain and an acidic box. Five FGFR genes that encode for multiple receptor protein variants are known. Alternative splicing of the FGFR2 mRNAs generates at least two known isoforms of the receptors, FGFR2IIIb and FGFR2IIIc.

Throughout the specification and the claims that follow, the term "FGFR2 specific" refers to any effector that has higher affinity ($K_D$<50 nM) or activity or binding to FGFR2 polypeptide or to the polynucleotide encoding same, than to another FGF receptor protein or polynucleotide. The effector can be any molecule including a ligand, an inhibitor, an antibody, a polypeptide, a polynucleotide or a small organic molecule such as a tyrosine kinase inhibitor. It is to be explicitly understood that the term "FGFR2 specific" does not exclude or preclude situations wherein the effector has some activity on another FGF receptor subtype. It is further to be understood that if the activity mediated via direct or indirect interaction with another receptor subtype is clinically important for the therapeutic utility observed, this is explicitly encompassed within the scope of the claimed invention.

The term "affinity" refers to the attraction between an antigen and an antibody which induces their binding. As used herein, by the term "antibody which has affinity for fibroblast growth factor receptor 2 (FGFR2) optionally with cross-reactivity to other FGF receptors" is meant that the antibody possesses high affinity to FGFR2 (KD<50 nM), but may also have affinity to other FGFRs. Preferably the antibody has an affinity of at least 10 nM for both FGFR2 and FGFR3. In some embodiments the affinity for FGFR2 and FGFR3 is approximately equal. In other embodiments the particular antibody may have a greater affinity for one or the other of these receptors.

By the term "substantially devoid of affinity to FGFR1" is meant that the antibody has low affinity to FGFR1 (KD>100 nM). A non-limiting example for an antibody which has high affinity for FGFR2 with cross-reactivity to other FGF receptors but is substantially devoid of affinity to FGFR1 is PRO-007 which has high affinity (KD<50 nM) to both FGFR2 and FGFR3 but low affinity to FGFR1.

As used herein, the terms "inhibitor" and "antagonist" are interchangeable and refer to a molecule, which attenuates, reduces or inhibits the activity or expression of at least one FGFR receptor subtype.

As used herein the term "ligand-dependent receptor activation" refers to activation of the FGF receptor that is dependent on the amount of ligand presented to the receptor. The term "ligand-independent receptor activation" or "constitutive receptor activation" refers to activation of the FGF receptor that is independent of ligand presentation. Receptors are usually activated by their corresponding ligand in a dose dependent manner. Certain mutations cause receptors to be constitutively activated independent of their ligand. For example the achondroplastic mutated form of FGFR3 causes ligand independent cell proliferation.

Many antibodies block only ligand-dependent receptor activation but not ligand-independent receptor activation. The antibodies of the present invention are unique in that they block both ligand-dependent and ligand-independent receptor activation.

One embodiment of the present invention is directed to molecules comprising an antigen binding domain which blocks both ligand-dependent and ligand-independent activation of FGFR2 and/or FGFR3.

As used herein "bladder cancer" or "urothelial cancer" refers to abnormal and or malignant cell growth in the bladder. Urothelial, or bladder cancer is the fourth most common cancer in the United States. About 90 percent of bladder cancers are transitional cell carcinomas, cancers that begin in the cells lining the bladder (Billerey et al., 2001). In some cases, cancer that begins in the transitional cells develops into invasive bladder cancer when it spreads through the lining of the bladder and invades the muscular wall of the bladder. Invasive cancer may grow through the bladder wall and spread to nearby organs. The muscle invasive tumors are associated with a high risk of metastases and a poor prognosis.

As used herein "osteosarcoma" refers to abnormal and or malignant bone growth. Osteosarcoma (osteogenic sarcoma) is the second most common primary bone tumor and is highly malignant. It is most common in people aged 10 to 20, although it can occur at any age. Osteosarcoma usually develops around the knee or in other long bones, particularly the metaphyses. It can metastasize, usually to lung or bone.

As used herein "breast cancer" refers to abnormal and or malignant cell growth in the breast. Most breast cancers are epithelial tumors that develop from cells lining ducts or lobules. Breast cancer invades locally and spreads initially through the regional lymph nodes, bloodstream, or both. Metastatic breast cancer may affect almost any organ in the body most commonly, lungs, liver, bone, brain, and skin. Most skin metastases occur in the region of the breast surgery; scalp metastases also are common.

In the US, cumulative risk of developing breast cancer is 12% (1 in 8) by age 95, and risk of dying of it is about 4%. Family history of breast cancer in a 1st-degree relative (mother, sister or daughter) doubles or triples risk of developing the cancer. About 5% of women with breast cancer carry a mutation in one of the 2 known breast cancer genes, BRCA1 or BRCA2. Men who carry a BRCA2 mutation also have an increased risk of developing breast cancer. Recent studies have demonstrated association between breast cancer and single nucleotide polymorphisms (SNPs) in FGFR2 (Hunter et al., 2007).

According to one aspect the present invention is related to a method of preventing, attenuating or treating a disease or disorder associated with FGFR2, comprising administering to a subject in need thereof a pharmaceutical composition comprising a therapeutically effective amount of an antibody specific to FGFR2 with cross-reactivity to other FGF receptors; and a pharmaceutically acceptable carrier. According to some embodiments the disease or disorder associated with FGFR2 is a cell proliferative disease or disorder including but not limited to bladder cancer, breast cancer, ovarian cancer, prostate cancer, osteosarcoma and chondrosarcoma.

Antibodies

Antibodies, or immunoglobulins, comprise two heavy chains linked together by disulfide bonds and two light chains, each light chain being linked to a respective heavy chain by disulfide bonds in a "Y" shaped configuration. Proteolytic digestion of an antibody yields Fv (Fragment variable) and Fc (fragment crystalline) domains. The antigen binding domains, Fab, include regions where the polypeptide sequence varies. The term F(ab')$_2$ represents two Fab' arms linked together by disulfide bonds. The central axis of the antibody is termed the Fc fragment. Each heavy chain has at one end a variable domain ($V_H$) followed by a number of constant domains ($C_H$). Each light chain has a variable domain ($V_L$) at one end and a constant domain ($C_L$) at its other end, the light chain variable domain being aligned with the variable domain of the heavy chain and the light chain constant domain being aligned with the first constant domain of the heavy chain (CH1).

The variable domains of each pair of light and heavy chains form the antigen-binding site. The domains on the light and heavy chains have the same general structure and each domain comprises four framework regions, whose sequences are relatively conserved, joined by three hypervariable domains known as complementarity determining regions (CDR1-3). These domains contribute specificity and affinity of the antigen-binding site.

In certain embodiments the present invention provides antibodies which block ligand-dependent and constitutive ligand-independent FGF receptor activation, comprising a $V_H$-CDR3 region (complementarity determining region 3 of the heavy chain) having a polypeptide sequence as set forth in SEQ ID NO: 1 and a corresponding $V_L$-CDR3 region (complementarity determining region 3 of the light chain) having a polypeptide sequence as set forth in SEQ ID NO:2. The corresponding polynucleotide sequences of the $V_H$-CDR3 and $V_L$-CDR3 regions are set forth in SEQ ID NO: 3 and SEQ ID NO: 4, respectively. The amino acid and nucleotide sequences are presented in Example 1.

Additionally, complementarity determining region (CDR) grafting may be performed to alter certain properties of the antibody molecule including affinity or specificity. A non-limiting example of CDR grafting is disclosed in U.S. Pat. No. 5,225,539.

The isotype of the heavy chain (gamma, alpha, delta, epsilon or mu) determines immunoglobulin class (IgG, IgA, IgD, IgE or IgM, respectively). The light chain is either of two isotypes (kappa, κ or lambda, λ) found in all antibody classes.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')$_2$ fragments. Further included within the scope of the invention are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies (see, for example, U.S. Pat. No. 4,816,567). Single chain antibodies fall within the scope of the present invention.

By the term "single chain variable fragment (scFv)" is meant a fusion of the variable regions of the heavy and light chains of immunoglobulin, linked together with a short (usually serine, glycine) linker. Single chain antibodies can be single chain composite polypeptides having antigen binding capabilities and comprising amino acid sequences homologous or analogous to the variable regions of an immunoglobulin light and heavy chain (linked $V_H$-$V_L$ or single chain Fv (scFv)). Both $V_H$ and $V_L$ may copy natural monoclonal antibody sequences or one or both of the chains may comprise a CDR-FR construct of the type described in U.S. Pat. No. 5,091,513, the entire contents of which are incorporated herein by reference. The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are incorporated herein by reference.

According to certain embodiments of the present invention, the antigen-binding portion of an antibody which has affinity for FGFR2 with cross-reactivity to other FGF receptors comprises a fragment of a monoclonal antibody such as the Fab, F(ab')$_2$ or a scFv fragments.

According to other embodiments of the present invention, the antibody fragment is a single chain Fv molecule (scFv) set forth in SEQ ID NO:5, having corresponding polynucleotide sequence SEQ ID NO:6. The respective polypeptide and polynucleotide sequences are presented in Example 1. The amino acid sequence (SEQ ID NO:7) and polynucleotide sequences (SEQ ID NO:8) of the scFv for PRO-001 are included herein for reference. Accordingly, the amino acid sequences for $V_H$-CDR3 and $V_L$-CDR3 of PRO-008 (SEQ ID NO:9 and SEQ ID NO: 10, respectively) and the corresponding polynucleotide sequences SEQ ID NO:11 and SEQ ID NO:12 are also included herein only for reference.

PEGylation is a process of attaching one or more chains of a fat polymer called polyethylene glycol (PEG) to a protein molecule. This process is intended to lengthen the life time of a substance in the bloodstream (without being metabolized and excreted by the body). The term "antibody" also includes modified formats of an antibody or its fragments i.e. PEGylated scFv or an antibody (or an antibody fragment) conjugated to a toxin molecule.

A "molecule having the antigen-binding portion of an antibody" as used herein is intended to include not only intact immunoglobulin molecules of any isotype and generated by any animal cell line or microorganism, but also the antigen-binding reactive fraction thereof, including, but not limited to, the Fab fragment, the Fab' fragment, the F(ab')$_2$ fragment, the variable portion of the heavy and/or light chains thereof, Fab mini-antibodies (see WO 93/15210, U.S. patent application Ser. No. 08/256,790, WO 96/13583, U.S. patent application Ser. No. 08/817,788, WO 96/37621, U.S. patent application Ser. No. 08/999,554, the entire contents of which are incorporated herein by reference), dimeric bispecific miniantibodies (see Muller et al., 1998) and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction. Such molecules may be provided by any known technique, including, but not limited to, enzymatic cleavage, peptide synthesis or recombinant techniques.

The term "Fc" as used herein refers to the constant portion of an immunoglobulin molecule (Fragment crystallizable) that mediates phagocytosis, triggers inflammation and targets Ig to particular tissues; the Fc portion is also important in complement activation.

In one embodiment of the invention, a chimera comprising a fusion of the extracellular domain of the RPTK and an immunoglobulin constant domain can be constructed useful in assaying for ligands of the receptor and in screening for antibodies and fragments thereof.

The "extracellular domain" when used herein refers to the polypeptide sequence of the FGFR2 disclosed herein which are normally positioned to the outside of the cell. The extracellular domain encompasses polypeptide sequences in which part of or all of the adjacent (C-terminal) hydrophobic transmembrane and intracellular sequences of the mature FGFR2 have been deleted. Thus, the extracellular domain-containing polypeptide can comprise the extracellular domain and a part of the transmembrane domain. According to some embodiments, the polypeptide comprises only the extracellular domain of the FGFR2. The truncated extracellular domain is generally soluble. The skilled practitioner can readily determine the extracellular and transmembrane domains of the FGFR2 by aligning it with known RPTK (receptor protein tyrosine kinases) amino acid sequences for which these domains have been delineated. Alternatively, the hydrophobic transmembrane domain can be readily delineated based on a hydrophobicity plot of the polypeptide sequence. The extracellular domain is N-terminal to the transmembrane domain.

The term "epitope" is meant to refer to that portion of any molecule capable of being bound by an antibody or a fragment thereof which can also be recognized by that antibody. Epitopes or antigenic determinants usually consist of chemically active surface groupings of molecules such as amino acids or sugar side chains and have specific three-dimensional structural characteristics as well as specific charge characteristics.

An "antigen" is a molecule or a portion of a molecule capable of being bound by an antibody. An antigen may have one or more than one epitope. The specific reaction referred to above is meant to indicate that the antigen will react, in a highly selective manner, with its corresponding antibody and not with the multitude of other antibodies which may be evoked by other antigens.

A "neutralizing antibody" as used herein refers to a molecule having an antigen-binding site to a specific receptor capable of reducing or inhibiting (blocking) activity or signaling through a receptor, as determined by in vivo or in vitro assays, as per the specification.

A "monoclonal antibody" or "nAb" is a substantially homogeneous population of antibodies to a specific antigen. mabs may be obtained by methods known to those skilled in the art. See, for example Kohler et al (1984) and U.S. Pat. No. 4,376,110 the contents of which are incorporated entirely herein by reference. The mAbs of the present invention may be of any immunoglobulin class including IgG, IgM, IgE, IgA, and any subclass thereof. A hybridoma producing a mAb may be cultivated in vitro or in vivo. High titers of mAbs can be obtained by in-vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

Chimeric antibodies are molecules, the different portions of which are derived from different animal species, such as those having a variable region derived from a murine mAb and a human immunoglobulin constant region. Antibodies which have variable region framework residues substantially from human antibody (termed an acceptor antibody) and complementarity determining regions substantially from a mouse antibody (termed a donor antibody) are also referred to as humanized antibodies. Chimeric antibodies are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Better et al, 1988; Cabilly et al, 1984; European Patent Applications 125023, 171496, 173494, 184187, 173494, PCT patent applications WO 86/01533, WO 97/02671, WO 90/07861, WO 92/22653 and U.S. Pat. Nos. 5,693,762, 5,693,761, 5,585,089, 5,530,101 and 5,225,539). These references are hereby incorporated by reference.

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

In yet another embodiment, the present invention provides molecules comprising at least the antigen-binding portion of an antibody which has affinity for FGFR2 optionally with cross-reactivity to other FGF receptors. These molecules include antibodies specific to FGFR2 and/or FGFR3, peptide analogs of such antibodies with binding affinity to the extracellular portion of FGFR2 and/or FGFR3, and peptidomimetics based on the structure of such peptides. The peptidomimetics of the invention may be similar in structure to AHNP, the small molecule form of an anti-HER2/neu peptidomimetic that has activity similar to the full monoclonal antibody Herceptin (Zhang et al., 2000).

Pharmacology

The present invention also contemplates pharmaceutical formulations, both for veterinary and for human medical use, which comprise as the active agent one or more molecules comprising at least the antigen-binding portion of an antibody which has affinity for FGFR2 optionally with cross-reactivity to other FGF receptors, for the manufacture of a therapeutic composition for the treatment or prophylaxis of the conditions variously described herein.

In such pharmaceutical and medicament formulations, the active agent is preferably utilized together with one or more pharmaceutically acceptable carrier(s) and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

Typically, the molecules of the present invention comprising the antigen binding portion of an antibody or comprising another polypeptide including a peptidomimetic will be suspended in a sterile saline solution for therapeutic uses. The pharmaceutical compositions may alternatively be formulated to control release of active ingredient (molecule comprising the antigen binding portion of an antibody) or to prolong its presence in a patient's system. Numerous suitable drug delivery systems are known and include, e.g., implantable drug release systems, hydrogels, hydroxymethylcellulose, microcapsules, liposomes, microemulsions, microspheres, and the like. Controlled release preparations can be prepared through the use of polymers to complex or adsorb the molecule according to the present invention. For example, biocompatible polymers include matrices of poly(ethylene-co-vinyl acetate) and matrices of a polyanhydride copolymer of a stearic acid dimer and sebaric acid (Sherwood et al, 1992). The rate of release of the molecule according to the present invention, i.e., of an antibody or antibody fragment, from such a matrix depends upon the molecular weight of the molecule, the amount of the molecule within the matrix, and the size of dispersed particles (Saltzman et al., 1989 and Sherwood et al., 1992).

The pharmaceutical composition of this invention may be administered by any suitable means, such as orally, topically, intranasally, subcutaneously, intramuscularly, intravenously, intra-arterially, intraarticulary, intralesionally or parenterally. Ordinarily, intravenous (i.v.), intraarticular, topical or parenteral administration will be preferred.

It will be apparent to those of ordinary skill in the art that the therapeutically effective amount of the molecule according to the present invention will depend, inter alia upon the administration schedule, the unit dose of molecule administered, whether the molecule is administered in combination with other therapeutic agents, the immune status and health of the patient, the therapeutic activity of the molecule administered and the judgment of the treating physician. As used herein, a "therapeutically effective amount" refers to the amount of a molecule required to alleviate one or more symptoms associated with a disorder being treated over a period of time.

Although an appropriate dosage of a molecule of the invention varies depending on the administration route, type of molecule (polypeptide, polynucleotide, organic molecule etc.) age, body weight, sex, or conditions of the patient, and should be determined by the physician in the end, in the case of oral administration, the daily dosage can generally be between about 0.01 mg to about 500 mg, preferably about 0.01 mg to about 50 mg, more preferably about 0.1 mg to about 10 mg, per kg body weight. In the case of parenteral administration, the daily dosage can generally be between about 0.001 mg to about 100 mg, preferably about 0.001 mg to about 10 mg, more preferably about 0.01 mg to about 1 mg, per kg body weight. The daily dosage can be administered, for example in regimens typical of 1-4 individual administration daily. Other preferred methods of administration include intraarticular administration of about 0.01 mg to about 100 mg per kg body weight. Various considerations in arriving at an effective amount are described, e.g., in Goodman and Gilman's: The Pharmacological Bases of Therapeutics, 8th ed., Pergamon Press, 1990; and Remington's Pharmaceutical Sciences, 17th ed., Mack Publishing Co., Easton, Pa., 1990.

The molecules of the present invention as active ingredients are dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. Other suitable carriers are well known to those skilled in the art. In addition, if desired, the composition can contain minor amounts of auxiliary substances such as wetting or emulsifying agents, pH buffering agents.

The combined treatment of one or more of the molecules of the invention with an anti-inflammatory drug such as methotrexate or glucocorticoids may provide a more efficient treatment for inhibiting FGFR2 activity. In one embodiment, the pharmaceutical composition comprises the antibody, an anti-inflammatory drug and a pharmaceutically acceptable carrier.

Polynucleotides

The term "nucleic acid" and "polynucleotides" refers to molecules such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

Within the scope of the present invention is a nucleic acid molecule encoding an antibody having affinity for FGFR2 optionally with cross-reactivity to other FGF receptors, which block receptor activation. The nucleic acid molecule contains a nucleotide sequence having at least 75% sequence identity, preferably about 90%, and more preferably about 95% identity to the above encoding nucleotide sequence set forth in any one of SEQ ID NO:3, SEQ ID NO:4 or SEQ ID NO:6 as would be well understood by those of skill in the art. In the hypervariable regions of the heavy chain and light chain, the nucleic acid molecule contains a nucleotide sequence having at least 50% sequence identity, preferably about 70% and more preferably about 80% identity to the molecule set forth in SEQ ID NO:6.

The invention also provides nucleic acids that hybridize under high stringency conditions to polynucleotides set forth in any one of SEQ ID NO:3, SEQ ID NO:4 or SEQ ID NO:6. or the complement thereof. As used herein, highly stringent conditions are those which are tolerant of up to about 5%-25% sequence divergence, preferably about 5%-15%. Without limitation, examples of highly stringent (−10° C. below the calculated Tm (temperature midpoint) of the hybrid) conditions use a wash solution of 0.1×SSC (standard saline citrate) and 0.5% SDS at the appropriate incubation temperature (Ti) below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5×Denhardt's reagent, 0.5% SDS, 100 µg/ml denatured, fragmented salmon sperm DNA at an appropriate incubation temperature Ti. See generally Sambrook et al., Molecular Cloning: A Laboratory Manual, 2d edition, Cold Spring Harbor Press (1989)) for suitable high stringency conditions.

Stringency conditions are a function of the temperature used in the hybridization experiment and washes, the molarity of the monovalent cations in the hybridization solution and in the wash solution(s) and the percentage of formamide in the hybridization solution. In general, sensitivity by hybridization with a probe is affected by the amount and specific activity of the probe, the amount of the target nucleic acid, the detectability of the label, the rate of hybridization, and the duration of the hybridization. The hybridization rate is maximized at a Ti (incubation temperature) of 20-25° C. below Tm for DNA:DNA hybrids and 10-15° C. below Tm for DNA:RNA hybrids. It is also maximized by an ionic strength of about 1.5M Na$^+$. The rate is directly proportional to duplex length and inversely proportional to the degree of mismatching.

Specificity in hybridization, however, is a function of the difference in stability between the desired hybrid and "background" hybrids. Hybrid stability is a function of duplex length, base composition, ionic strength, mismatching, and destabilizing agents (if any).

The Tm of a perfect hybrid may be estimated for DNA:DNA hybrids using the equation of Meinkoth et al (1984), as $$Tm=81.5° C.+16.6(\log M)+0.41(\% GC)-0.61(\% form)-500/L$$

and for DNA:RNA hybrids, as $$Tm=79.8° C.+18.5(\log M)+0.58(\% GC)-11.8(\% GC)^2-0.56(\% form)-820/L$$

where
- M, molarity of monovalent cations, 0.01-0.4 M NaCl,
- % GC, percentage of G and C nucleotides in DNA, 30%-75%,
- % form, percentage formamide in hybridization solution, and
- L, length hybrid in base pairs.

Tm is reduced by 0.5-1.5° C. (an average of 1° C. can be used for ease of calculation) for each 1% mismatching. The Tm may also be determined experimentally. As increasing length of the hybrid (L) in the above equations increases the Tm and enhances stability, the full-length rat gene sequence can be used as the probe.

Filter hybridization is typically carried out at 68° C., and at high ionic strength (e.g., 5-6×SSC), which is non-stringent, and followed by one or more washes of increasing stringency, the last one being of the ultimately desired high stringency. The equations for Tm can be used to estimate the appropriate Ti for the final wash, or the Tm of the perfect duplex can be determined experimentally and Ti then adjusted accordingly.

The invention also provides for conservative amino acid variants of the molecules. Variants according to the invention also may be made that conserve the overall molecular structure of the encoded proteins. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

Having now fully described this invention, it will be appreciated by those skilled in the art that the same can be performed within a wide range of equivalent parameters, concentrations, and conditions without departing from the spirit and scope of the invention and without undue experimentation. The principles of the invention may be better understood with reference to the non-limiting examples below.

EXAMPLES

Example 1

Generation and Sequences of Antibodies

Screening for Antibodies

The antibodies PRO-001 (which binds only FGFR3 with high affinity) and PRO-008 (which binds both FGFR1 and FGFR3 with high affinity) serve merely as reference to PRO-007 (which binds both FGFR2 and FGFR3 with high affinity). The generation of PRO-001 and PRO-008 was described in WO 2002/102972. Fabs from the Human Combinatorial Antibody Library (HuCAL®) developed at MorphoSys (Munich, Germany), were screened for affinity to a soluble dimeric form of the extracellular domain of the FGFR3 receptor (screening strategies are disclosed in WO 97/08320, U.S. Pat. No. 6,300,064, and Knappik et al., (2000), the entire contents of which are incorporated herein by reference). Soluble dimeric forms of a FGFR can be constructed and prepared in a number of different ways. For instance, the extracellular domain of a FGFR joined to Fragment crystalline (Fc) and expressed as a fusion polypeptide that dimerizes naturally by means of the Fc portion of the FGFR-Fc fusion.

PRO-007 single chain (sc) presented hereafter as SEQ ID NO: 5 was generated from PRO-001 sc (SEQ ID NO: 7) by point mutations in the complementarity determining region 3 of the variable domain in the light chain ($V_L$-CDR3). The antibody fragment was then tested for receptor specificity and inhibition of cell proliferation.

Additional antibodies generated from PRO-007 by point mutations also demonstrated high binding affinity to both FGFR2 and FGFR3. For example antibody IB1, the $V_H$ of which is presented hereafter in SEQ ID NO: 13 (generated by three point mutations in the $V_H$ of PRO-007), binds both FGFR2 and FGFR3 with high affinity similar to PRO-007. CDRs are bold and underlined. The first two mutations are designated with larger letters, and the third point mutation is a stop codon after the CDR SYYPDFD (SEQ ID NO: 14).

Antigen Binding Sequences of the Antibodies

| Clone | VH-CDR3 Sequence | VH-CDR3 Nuc. Sequence | VL-CDR3 Sequence | VL-CDR3 Nuc. Sequence |
|---|---|---|---|---|
| PRO-007 | SYYPDFDY (SEQ ID NO: 1) | TCTTATTATCCTG ATTTTGATTAT (SEQ ID NO: 3) | QSYASQGIHY (SEQ ID NO: 2) | CAGTCTTATGCTT CTCAGGGTAT TCATTAT (SEQ ID NO: 4) |

PRO-007 SINGLE CHAIN (SEQ ID NO: 5)

MVQLQQSGPGLVKPSQTLSLTCAISGDSVSSNSAAWNWIRQSPGRGLEWLGRTYYRSKW
YNDYAVSVKSRITINPDTSKNQFSLQLNSVTPEDTAVYYCARSYYPDFDYWGQGTLVTV
SSAGGGSGGGGSGGGGSGGGGSDIELTQPPSVSVAPGQTARISCSGDALGDKYASWYQQ
KPGQAPVLVIYDDSDRPSGIPERFSGSNSGNTATLTISGTQAEDEADYYCQSYASQGIH
YVFGGGTKLTVLGQ

Polynucleotide sequence encoding PRO-007 SINGLE CHAIN (SEQ ID NO: 6)

ATGGTGCAATTGCAACAGTCTGGTCCGGGCCTGGTGAAACCGAGCCAAACCCTGAGCCT
GACCTGTGCGATTTCCGGAGATAGCGTGAGCAGCAACAGCGCGGCGTGGAACTGGATTC
GCCAGTCTCCTGGGCGTGGCCTCGAGTGGCTGGGCCGTACCTATTATCGTAGCAAATGG
TATAACGATTATGCGGTGAGCGTGAAAAGCCGGATTACCATCAACCCGGATACTTCGAA
AAACCAGTTTAGCCTGCAACTGAACAGCGTGACCCCGGAAGATACGGCCGTGTATTATT
GCGCGCGTTCTTATTATCCTGATTTTGATTATTGGGGCCAAGGCACCCTGGTGACGGTT
AGCTCAGCGGGTGGCGGTTCTGGCGGCGGTGGGAGCGGTGGCGGTGGTTCTGGCGGTGG
TGGTTCCGATATCGAACTGACCCAGCCGCCTTCAGTGAGCGTTGCACCAGGTCAGACCG
CGCGTATCTCGTGTAGCGGCGATGCGCTGGGCGATAAATACGCGAGCTGGTACCAGCAG
AAACCCGGGCAGGCGCCAGTTCTGGTGATTTATGATGATTCTGACCGTCCCTCAGGCAT
CCCGGAACGCTTTAGCGGATCCAACAGCGGCAACACCGCGACCCTGACCATTAGCGGCA
CTCAGGCGGAAGACGAAGCGGATTATTATTGCCAGTCTTATGCTTCTCAGGGTATTCAT
TATGTTTGGCGGCGGCACGAAGTTAACCGTTCTTGGCCAGTGA

PRO-001 SINGLE CHAIN (SEQ ID NO: 7)

MVQLQQSGPGLVKPSQTLSLTCAISGDSVSSNSAAWNWIRQSPGRGLEWLGRTYYRSKW
YNDYAVSVKSRITINPDTSKNQFSLQLNSVTPEDTAVYYCARSYYPDFDYWGQGTLVTV
SSAGGGSGGGGSGGGGSGGGGSDIELTQPPSVSVAPGQTARISCSGDALGDKYASWYQQ
KPGQAPVLVIYDDSDRPSGIPERFSGSNSGNTATLTISGTQAEDEADYYCQSYDGPDLW
VFGGGTKLTVLGQ

Polynucleotide sequence encoding PRO-001 SINGLE CHAIN (SEQ ID NO: 8)

ATGGTGCAATTGCAACAGTCTGGTCCGGGCCTGGTGAAACCGAGCCAAACCCTGAGCCT
GACCTGTGCGATTTCCGGAGATAGCGTGAGCAGCAACAGCGCGGCGTGGAACTGGATTC
GCCAGTCTCCTGGGCGTGGCCTCGAGTGGCTGGGCCGTACCTATTATCGTAGCAAATGG
TATAACGATTATGCGGTGAGCGTGAAAAGCCGGATTACCATCAACCCGGATACTTCGAA
AAACCAGTTTAGCCTGCAACTGAACAGCGTGACCCCGGAAGATACGGCCGTGTATTATT
GCGCGCGTTCTTATTATCCTGATTTTGATTATTGGGGCCAAGGCACCCTGGTGACGGTT
AGCTCAGCGGGTGGCGGTTCTGGCGGCGGTGGGAGCGGTGGCGGTGGTTCTGGCGGTGG
TGGTTCCGATATCGAACTGACCCAGCCGCCTTCAGTGAGCGTTGCACCAGGTCAGACCG
CGCGTATCTCGTGTAGCGGCGATGCGCTGGGCGATAAATACGCGAGCTGGTACCAGCAG
AAACCCGGGCAGGCGCCAGTTCTGGTGATTTATGATGATTCTGACCGTCCCTCAGGCAT
CCCGGAACGCTTTAGCGGATCCAACAGCGGCAACACCGCGACCCTGACCATTAGCGGCA
CTCAGGCGGAAGACGAAGCGGATTATTATTGCCAGAGCTATGACGGTCCTGATCTTTGG
GTGTTTGGCGGCGGCACGAAGTTAACCGTTCTTGGCCAGTGA

| Clone | VH-CDR3 Sequence | VH-CDR3 Nuc. Sequence | VL-CDR3 Sequence | VL-CDR3 Nuc. Sequence |
|---|---|---|---|---|
| PRO-008 | NMAYTNYQ YVNMPHFDY (SEQ ID NO: 9) | AATATGGCTTA TACTAATTATC AGTATGTTAAT ATGCCTCATTT TGATTAT (SEQ ID NO: 11) | QSYDYFKL (SEQ ID NO: 10) | CAGAGCTATG ACTATTTTAA GCTT (SEQ ID NO: 12) |

PRO-IB1 VH (SEQ ID NO: 13)

VQLQQSGPGLVKPSQTLSLTCAISGDSVSSNSAAWS WIRQSPGRGLEWLGRTYYRSKWY

NDYAVSVKSRITINPDTSKNQFSLQLN G VTPEDTAVYYCARSYYPDFDWGQGTLVTVSS

Example 2

Antibody—Receptor Binding

AssayMaxiSorp ELISA plates were coated with 100 μl anti-human Fc (10 μg/ml) in bicarbonate overnight at 4° C. Wells were washed five consecutive times with a PBS solution containing 0.1% Tween 20 (PBST). The well surface was blocked with 250 μl PBST+3% BSA (blocking solution) for 1 hour at 37° C. This was followed by capturing 1 μg of fragment crystalline (Fc) fusion of the extracellular domain of FGF receptor (FGFR/Fc) for 1 hour at room temperature. To assess the antibody binding to the captured FGFR/Fc, 1 μg each of the tested Fabs was incubated in 100 μl blocking solution per well for 1 hour at room temperature. Wells were then washed 5 times with PBST. Reaction was initiated with the addition of 100 μl of 0.8 μg/ml goat anti-human Fab-HRP in blocking solution, subsequently washed and detected with TMB substrate (Pierce). The absorbance was measured at 450 nm.

Figure 1B:
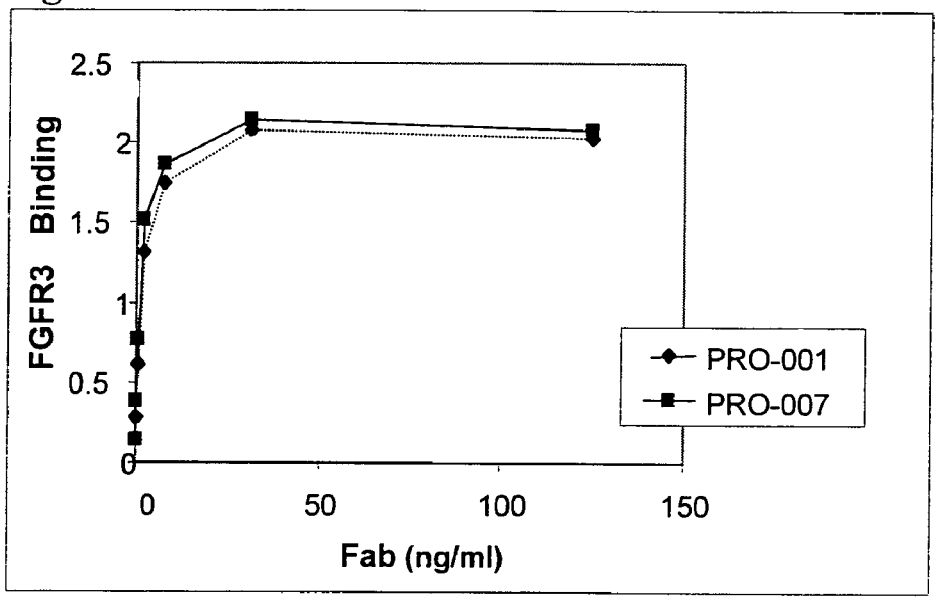
Figure 1C:
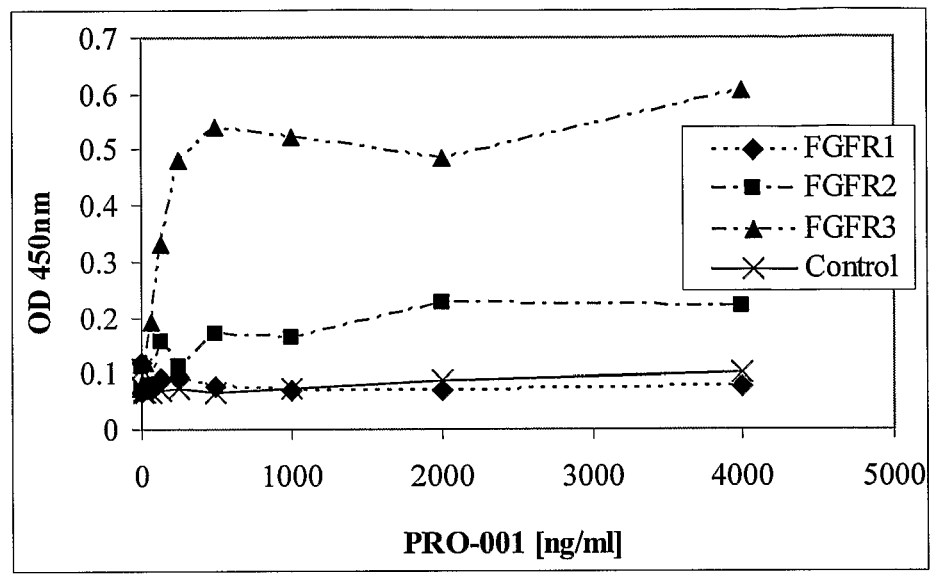
Figure 1D:
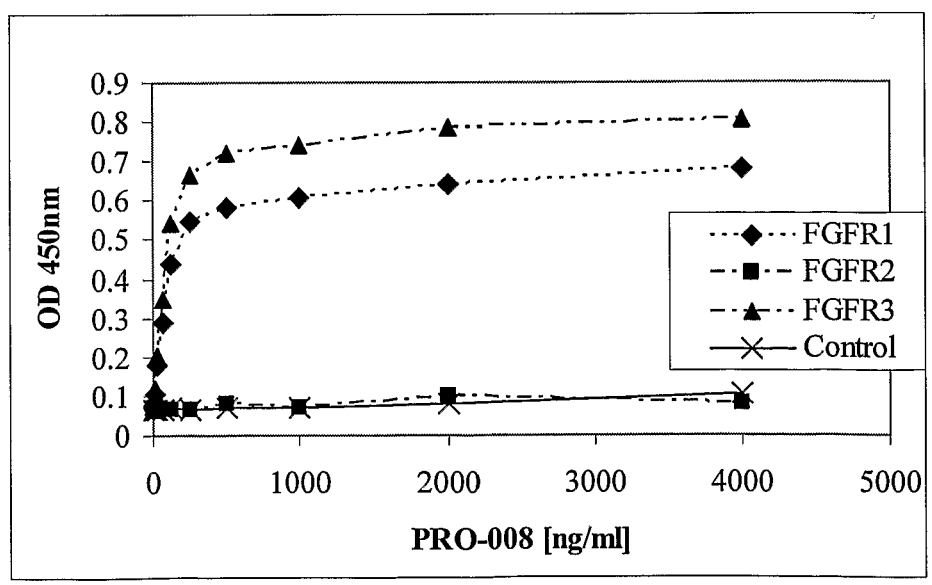

Fortin et al. (2005) teach that the antibody PRO-007 binds only FGFR2 with high affinity, however, FIGS. 1A and 1B demonstrate that PRO-007 binds both FGFR2 and FGFR3 with high affinity. PRO-001 binds only FGFR3 with high affinity (and FGFR2 with low affinity). PRO-008 binds both FGFR1 and FGFR3 with high affinity (FIGS. 1C and D).

Example 3

Inhibition of Mitogen-Activated Protein Kinase (MAPKinase) by Various Antibodies mKlotho stable clone 09 HEK293 cells (Human Embryonic Kidney cells) were grown to a final concentration of 200,000 cells/well in a 24 well plate and incubated at 37° C. 5% CO2 until they attached to the plate. The following day, cells were starved in Dulbecco Modified Eagle's Minimal Essential Medium (DMEM-Gibco-California, USA) for 4 hours and then incubated with 0.5 ml DMEM containing 20 μg/ml of either one of the antibodies PRO-001, PRO-007 and PRO-008 (the antigen binding sequences of which are presented in Example 1) or PRO-000 (a control antibody which lacks the VL-CDR3) for 20 minutes at 37° C. 5% CO2. FGF23 (50 μl of a solution of 10 μg/ml ProChon Biotech Ltd., Rehovot, Israel) was then added to each well to reach a final concentration of 10 ng/ml, and the reaction was incubated for 5 additional minutes at 37° C. 5% CO2. Then, the reaction was stopped by draining all the media and lysing the cells with 200 μl 2× Loading buffer (Tris ICN Glycine SDS BioLab, Jerusalem, Israel). The lysates were transferred to tube and heated for 5 minutes at 95° C. Lysate samples were analyzed by 13% sodium dodecyl sulfate-polyacrylamide gel electrophoresis (SDS PAGE).

TABLE 1

Antibody induced inhibition of MAPKinase Phosphorylation:

| Antibody | FGF23 | MAPKinase Phosphorylation |
|---|---|---|
| — | + | + |
| PRO-000 | + | + |
| PRO-001 | + | + |
| PRO-007 | + | − |
| PRO-008 | + | + |
| PRO-000 + 001 + 007 + 008 | − | − |
| PRO-000 + 001 + 007 + 008 | + | − |

Example 4

Inhibition of Cell Proliferation Using PRO-007

FDCP Cell Line

The FDCP cell line is a murine immortalized, interleukin 3 (IL3) dependent cell line of myelocytic bone marrow origin, which does not express endogenous FGF Receptors (FGFR). Upon transfection with FGFR cDNA and stable expression of the encoded receptor, the FDCP cell line exhibits an FGF dose dependent proliferative response that can replace the dependence on IL3. FDCP cell lines, expressing FGFRs can therefore be used to screen for specific inhibitors or activators of FGFR, as well as for analyzing FGFR signaling.

FDCP Cell Proliferation Assay

FDCP cells expressing FGFR1, FGFR2, FGFR3 or FGFR4 were grown in "full medium" (Iscove's Medium containing 2 ml glutamine, 100 μg/ml penicillin, 100 μg/ml streptomycin, 12.5 μg/ml Nystatin and 10% FBS, Gibco, California, USA) supplemented with 5 μg/ml heparin and 10 ng/ml FGF9. Cells were split every 3 days and kept in culture no more than one month. One day prior to the experiment, the cells were split. Before the experiment, the cells were washed 3 times (1000 rpm, 6 min) with full medium. Later, the cells were resuspended and counted with Trypan Blue (Sigma). Twenty thousand (20,000) cells/well were added to wells in a 96-well plate in 50 μl in full medium containing 5 μg/ml heparin. Conditioned medium was added in an additional volume of 50 μl full medium containing FGF9 at varying concentrations to a final volume of 100 μl. A primary stock solution of the antibody (containing twice the amount of the highest antibody concentration) was prepared in Iscove's medium containing 5 μg/ml heparin and 2.5 ng/ml FGF or IL-3. The stock solution was filtered through a pre-blocked 0.2 μm syringe nitrocellulose filter, and serial 2 fold antibody dilutions were prepared. Dilutions were kept on ice until use. 50 μl of the antibody containing solution was added to each well and the plate was incubated at 37° C. for either 40 hours or 64 hours.

After incubation, the reaction was developed as follows: 100 μl of activator solution was added to 5 ml XTT reagent and mixed gently. 50 μl of mixture was added to each well. Optical density (OD) at 490 nm at this point gave the zero time reading. Cells were then incubated at 37° C. for 4 hours (in the case of 40 hours incubation) or 2 hours (for the 64 hours incubation) and proliferation was measured by O.D. at 490 nm (A490).

It is noted that the assay is successful when the O.D. of untreated control growing with saturated amounts of FGF (10 and 20 ng/ml) is at least 1.3 O.D. units. Furthermore, it is noted that the background of wells with no cells should be 0.2-0.35 O.D. units and that the O.D. absorbance of 1.25 ng/ml FGF9 should not be less than 40% of the O.D. absorbance achieved with saturated FGF 9 concentration (10 and 20 ng/ml). Specific inhibition of FGF and FGF receptor mediated proliferation should always be accompanied with lack of any inhibition of the same antibody concentration on IL-3 dependent cell proliferation.

The following FDCP cell lines were used:

FDCP-FR1: FDCP cells transfected with the human wild-type FGFR1.

FDCP-FR2: FDCP cells transfected with the human wild-type FGFR2.

FDCP-FR3: FDCP cells transfected with the human wild-type FGFR3.

FDCP-FR4: FDCP cells transfected with the human wild-type FGFR4.

Neutralizing Activity of PRO-007

Figure 2:
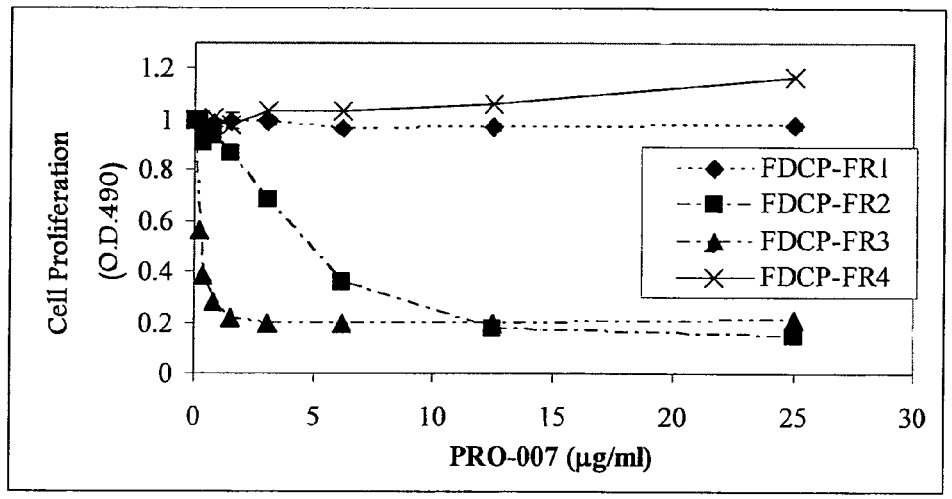
FIG. 2. PRO-007 inhibits proliferation of FDCP cells transfected with either FGFR2 or FGFR3, but not of FDCP cells transfected with either FGFR1 or FGFR4.

The neutralizing activity of the antibodies was measured by the aforementioned cell proliferation analysis in FDCP-FR1, FDCP-FR2, FDCP-FR3 and FDCP-FR4 cell lines. Increasing amounts of the PRO-007 scFv were added to FDCP-FR1 (diamond ♦), FDCP-FR2 (square ■), FDCP-FR3 (closed triangle ▲), and FDCP-FR4 (X) grown in the presence of FGF9 (FIG. 2). Two days later, an XTT proliferation assay was performed. FIG. 2 demonstrates that PRO-007 scFv inhibited FDCP-FR2 and FDCP-FR3 cell proliferation, however, it had no effect on FDCP-FR1 and FDCP-FR4 cell proliferation.

Example 5

Inhibition of Ligand-Dependent and Constitutive Ligand-Independent Receptor Activation FDCP cell Lines Expressing Wild Type and Mutant FGFR3

As previously described, FDCP cells do not express endogenous FGF Receptors (FGFR). FDCP cells were transfected with either wild type FGFR3 (WT) which has ligand-dependent activation, or with mutant FGFR3 (S249C and E650K) which are activated independently of the ligand (ligand-independent activation).

Neutralizing Activity of PRO-007 vs. PRO-001

Figure 3:
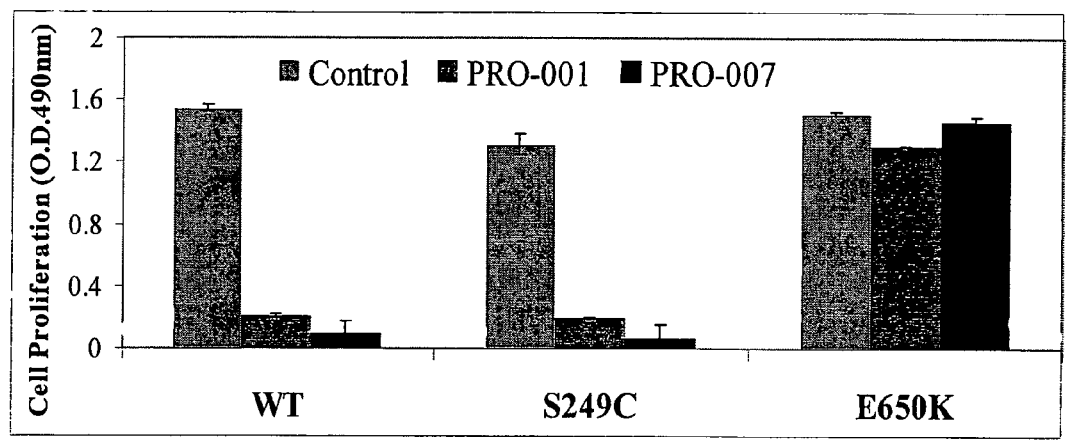
FIG. 3. PRO-001 and PRO-007 inhibit proliferation of FDCP cells transfected with either wild-type (ligand-dependent) FGFR3 (WT) or constitutively activated FGFR3 mutant (S249C), but not of FDCP cells transfected with the intracellular mutant (E650K).

Cell proliferation assay was performed as previously described in example 4. In FDCP cells transfected with wild type FGFR3 (WT), both PRO-001 and PRO-007 markedly inhibited cell proliferation, however, PRO-007 had a stronger effect. In FDCP cells transfected with constitutively activated FGFR3 mutant (S249C), again both PRO-001 and PRO-007 significantly inhibited cell proliferation, with PRO-007 having a stronger effect. However, in FDCP cells transfected with a different constitutively activated FGFR3 mutant (E650K), PRO-001 and PRO-007 had no effect on cell proliferation (FIG. 3)

Example 6

Bladder Carcinoma Cell Lines 5637 (DSMZ) human bladder carcinoma; grade II
SW780 (DSMZ) human transitional cell carcinoma grade I
RT112 (DSMZ) human transitional bladder carcinoma, grade II
J82 (ATCC) human transitional bladder carcinoma
RT-4 (DSMZ) human transitional bladder carcinoma established from a recurrent well-differentiated transitional papillary tumor of the urinary bladder (clinical stage T2, histological grade G1.

Example 7

Anti-FGFR2 Antibody Inhibits Proliferation in Human Bladder Cancer Cell Lines

The bladder carcinoma RT112 cell line, which expresses the wild-type receptor, was obtained from the DSMZ (Deutsche Sammlung von Mikroorganismen und Zellkulturen GmbH—German Collection of Microorganisms and Cell Cultures). The ability of PRO-001 antibody (with high affinity only to FGFR3), and PRO-007 antibody (with high affinity to both FGFR2 and FGFR3) to inhibit RT112 cell proliferation was tested.

Figure 4:
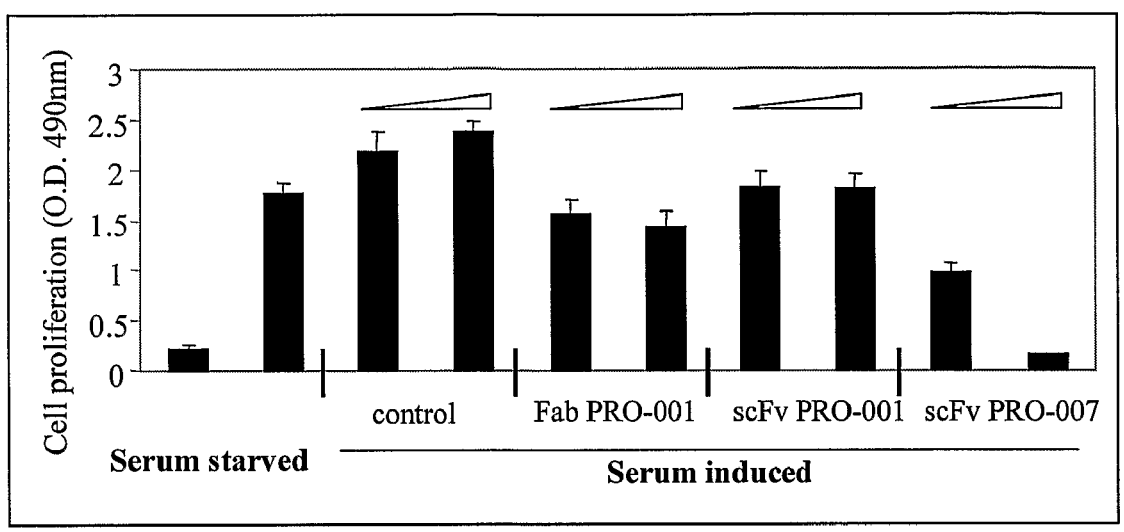
FIG. 4. Proliferation of bladder carcinoma RT112 cells was completely blocked upon treatment with PRO-007 scFv (antibody with affinity to both FGFR2 and FGFR3) but only partially inhibited by treatment with PRO-001 Fab or scFv (an anti-FGFR3 specific antibody).

The cells were seeded at 1000 or 2000 cells/well in a 96 well plate and cultured with 10% FCS or with FGF1/heparin. RT112 cells were then exposed to either of the antibodies PRO-007 scFv or PRO-001 scFv. In contrast to the slight inhibition observed with PRO-001, PRO-007 scFv completely blocked RT112 cell proliferation at 150 µg/ml (FIG. 4).

When PRO-001 scFv was added to the cells at the time of cell seeding, there was still no effect on the RT112 proliferation rate (not shown).

Figure 5A:
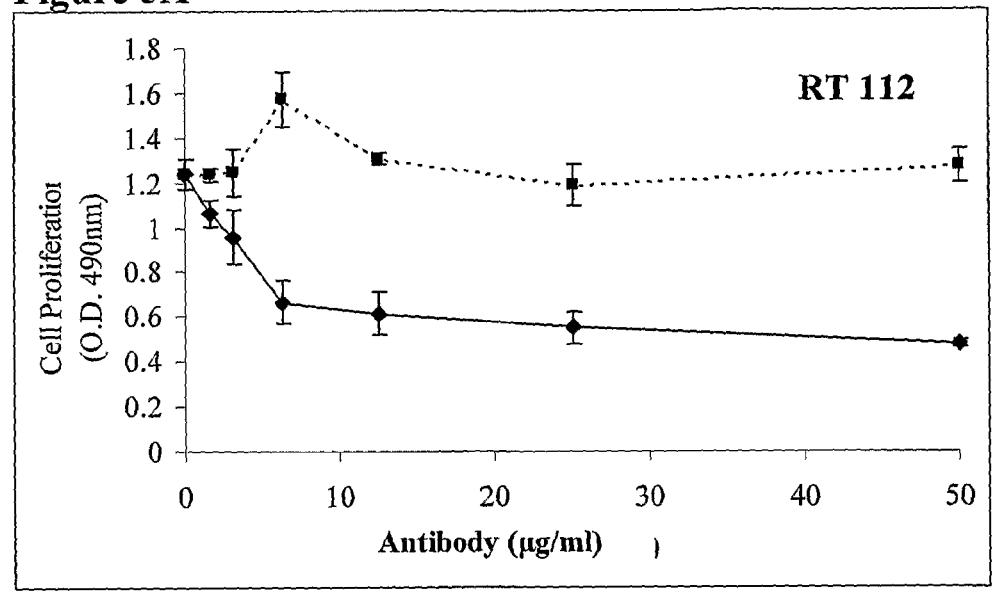
FIG. 5. PRO-007 specifically blocks proliferation of bladder carcinoma RT112 cells (A), but not of bladder carcinoma J82 cells (B).

To determine the effective dose of PRO-007 scFv, increasing levels of the single chain were added to RT12 cells. A clear dose response on cell proliferation was observed with minimal effect at 9 µg/ml and complete block at 150 µg/ml (FIG. 5A).

Figure 5B:
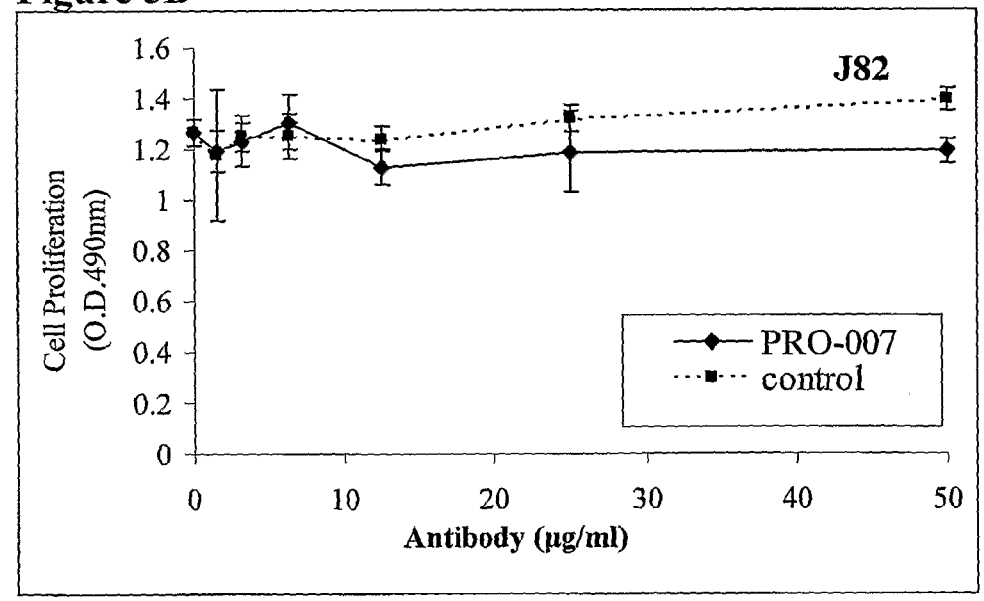
Figure 6A:
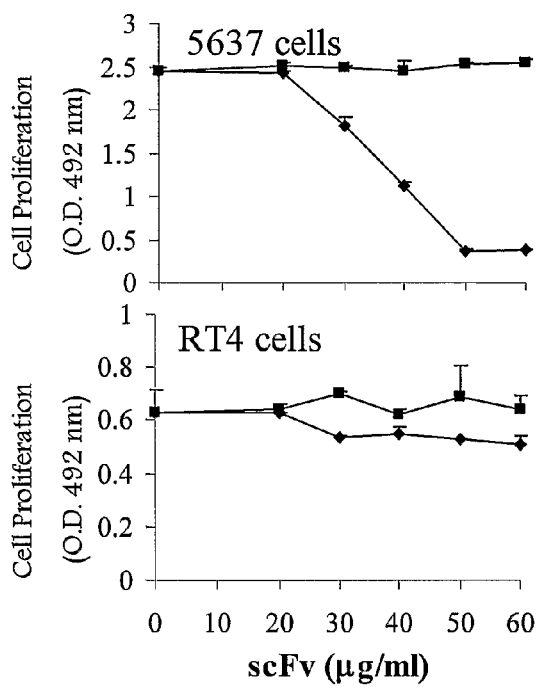
FIG. 6. PRO-007 single chain (sc) blocks cell proliferation in 5637 bladder carcinoma cells (A) and in Jon cells (B) but not in SW780 and RT4 cell lines (C and D, respectively).
Figure 6B:
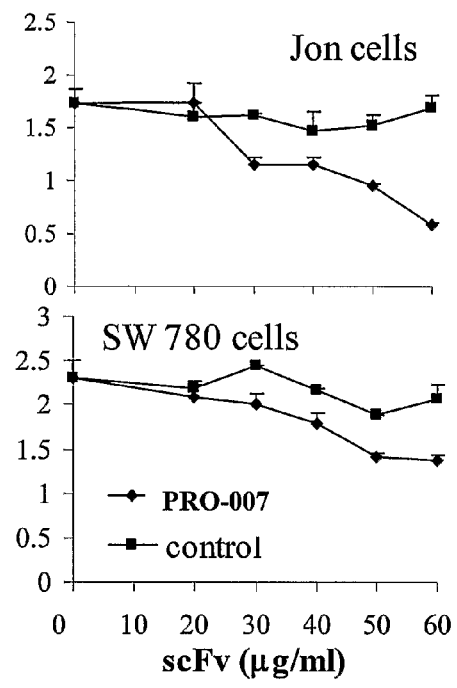

To show the specificity of the observed effect, we added PRO-007 scFv to the J82 bladder carcinoma cell line that harbors a $FGFR3^{K650E}$ activated receptor. PRO-007 had no effect on J82 cell proliferation demonstrating the specificity of its action on RT112 cells (FIG. 5B).

PRO-007 sc Activity in Other Bladder Carcinoma Cell Lines

The SW780, 5637, RT4 and Jon TCC cell lines were seeded at a concentration of about 2000 cells/well in a 96 well plate. The next day, PRO-007 scFv or a control scFv were added at increasing concentrations. Five days later, cell proliferation was measured by XTT showing a dose dependent proliferation arrest of 5637 and Jon but not of SW780 and RT4 cell lines (FIG. 6A-D).

Activity of PEGylated PRO-007 scFv

Figure 7:
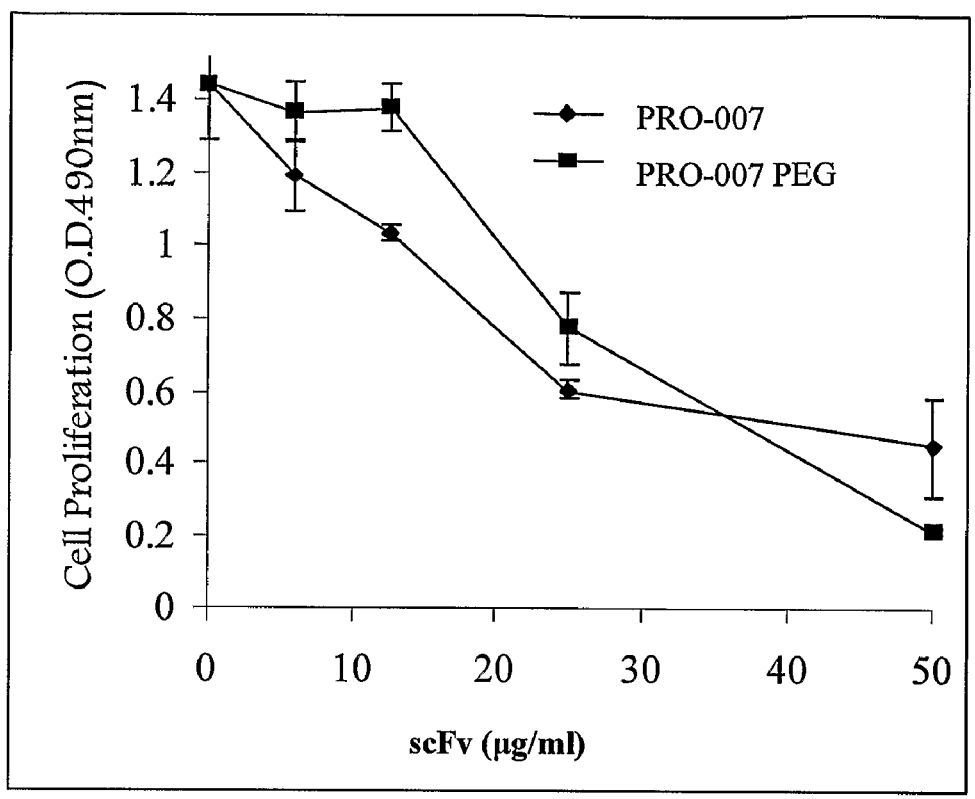
FIG. 7. Neutralizing activity of PRO-007 scFv and PEGylated PRO-007 scFv.

RT112 cells were incubated with PEGylated or non-PEGylated PRO-007 scFv. The inhibitory effect of the PEGylated PRO-007 scFv was demonstrated to match that of the non-modified single chain (FIG. 7).

Relative Expression of FGFRs in Bladder Carcinoma Cell Lines

Figure 8:
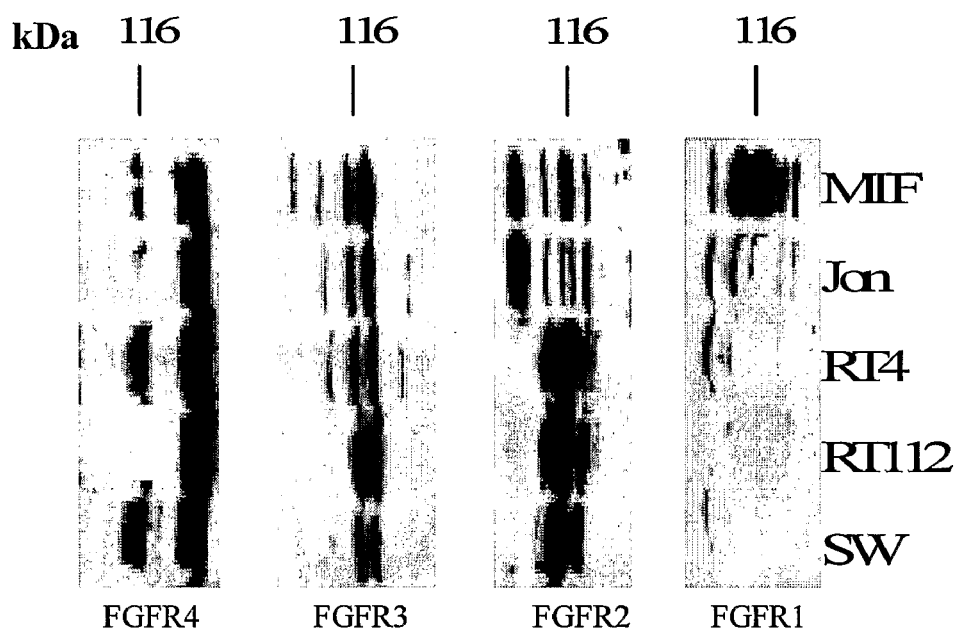
FIG. 8. Expression of FGFRs in bladder carcinoma cell lines. The indicated cell lines were lysed and probed with either anti-FGFR1, anti-FGFR2, anti-FGFR3 or anti-FGFR4.

The relative expression levels of FGFRs in RT112, 5637, RT4, Jon and SW780 were analyzed by Western blot analysis (FIG. 8). This demonstrated low or undetectable FGFR1 expression and moderate or high expression of FGFR2 and FGFR3 in all lines as compared to primary articular chondrocytes.

FGF-Induced Signal Transduction in RT112 Cells

Figure 9:
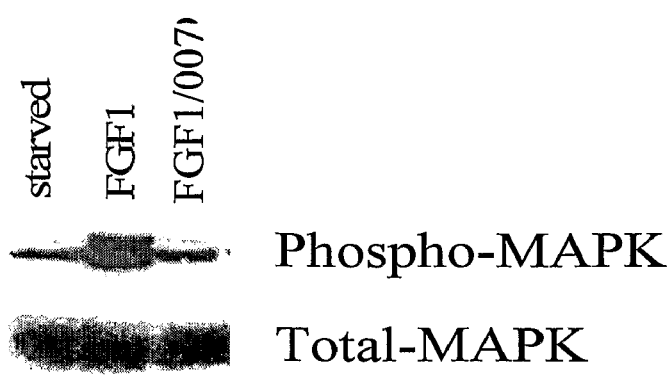
FIG. 9. PRO-007 scFv blocks FGF-induced MAPK in RT112 cells.

Serum starved RT112 cells were pre-incubated 20 minutes with 150 µg/ml PRO-007 scFv and then stimulated 5 minutes with 100 ng/ml FGF1. Pre-incubation with PRO-007 scFv completely blocked ERK1 and 2 activation by FGF1 as judged by Western with anti-phospho MAPK antibodies (FIG. 9).

Example 8

Inhibition of Osteosarcoma Cell Proliferation

SAOA2 and SJSA are two Osteosarcoma cell lines. Osteosarcoma SAOA2 cells were cultured in Dulbecco Modified Eagle's Minimal Essential Medium (DMEM-Gibco, California, USA)+10% FCS and SJSA cells were cultured in Roswell Park Memorial Institute medium (RPMI Gibco, California, USA)+10% FCS. Cells were seeded in a concentration of 2000 cells per well in a 96 well plate and incubated with the antibodies for 4 days. Antibody containing medium was replaced once. Cell proliferation was measured using the XTT assay).

Figure 10A:
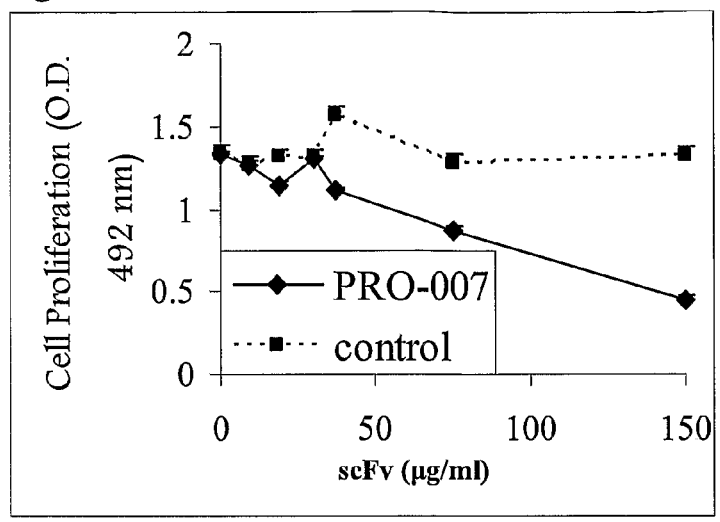
FIG. 10. PRO-007 inhibits proliferation of Osteosarcoma SAOA2 cells (A). Both PRO-007 and PRO-001 inhibit proliferation of SAOA2 cells (B)
Figure 10B:
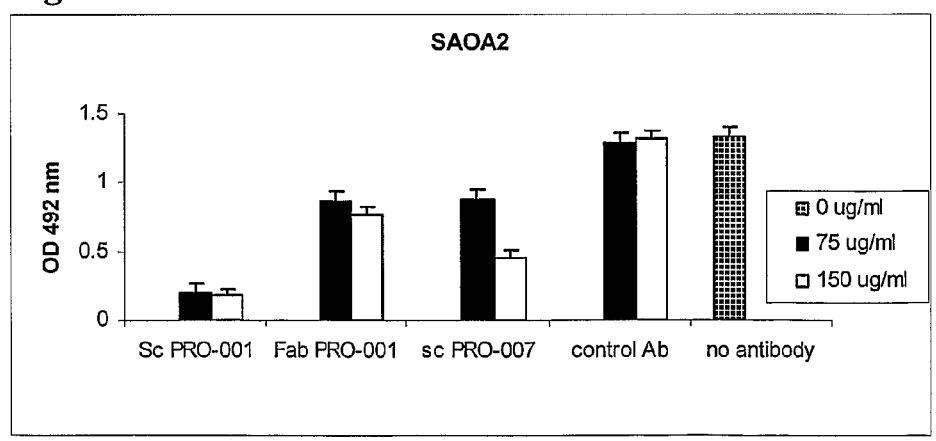
Figure 11A:
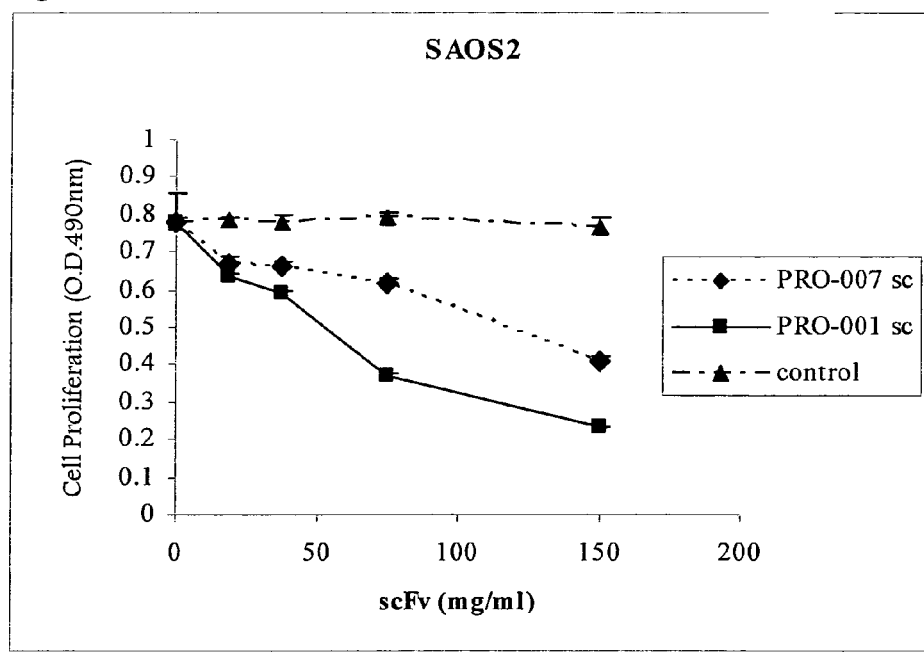
FIG. 11. PRO-007 and PRO-001 inhibit proliferation of SAOA2 cells (A). PRO-007 and PRO-001 inhibit proliferation of Osteosarcoma SJSA1 cells (B).
Figure 11B:
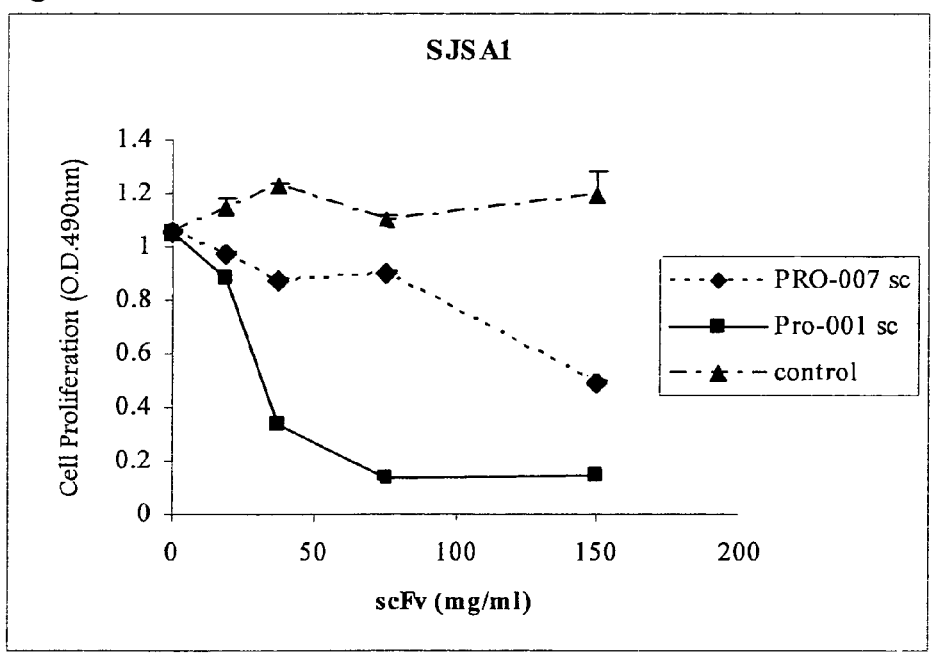

Relative to untreated cells, treatment with single chain Fv of PRO-007 significantly inhibited cell proliferation in SAOA2 cell line (FIG. 10A). FIG. 10B demonstrates that PRO-007 scFv, PRO-001 scFv and PRO-001 Fab all inhibit cell proliferation in SASO2 cells. FIG. 11A again shows a marked inhibition of SASO2 cell proliferation by PRO-007 scFv and an even more pronounced inhibition by PRO-001 scFv. In SJSA1 cells there was significant inhibition of cell proliferation with a stronger inhibition by PRO-001 scFv (FIG. 11B).

In different cell lines FGFR2 and FGFR3 have varying significance with respect to cell proliferation. In Bladder cancer cell lines FGFR2 is more important for cell proliferation while in Osteosarcoma cell lines FGFR3 is more important for cell proliferation.

Example 9

Antibody Binding to Heparin Binding Domain

Figure 12:
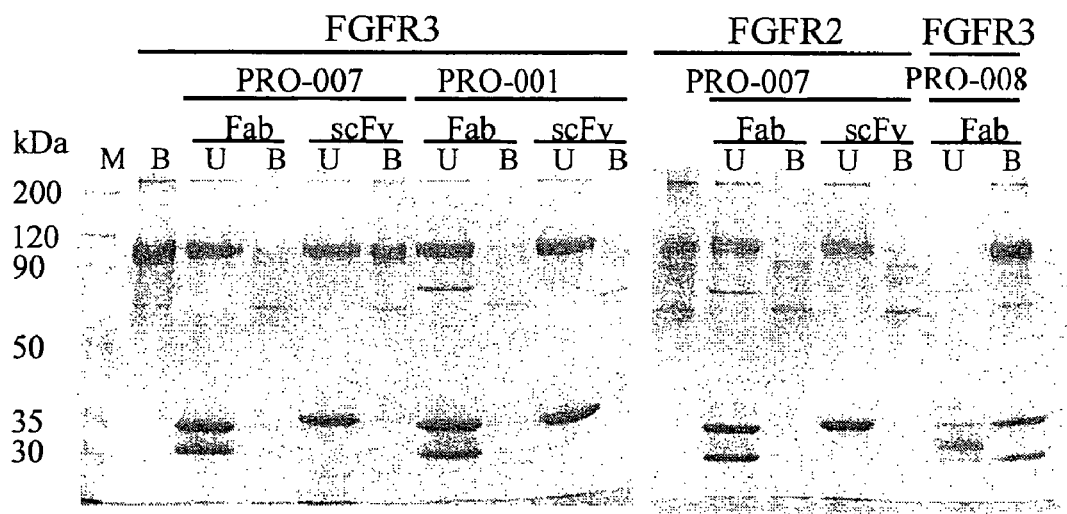
FIG. 12. FGFR3 appears only in the heparin Sepharose unbound fraction (U) when either PRO-001 or PRO-007 are present, indicating that these antibodies compete with heparin; FGFR3 remains heparin bound (B) in the presence of control antibody PRO-008 Fab. In addition to FGFR3PRO-007 also binds to FGFR in the heparin binding domain and blocks heparin binding.

PRO-007, PRO-001 and PRO-008 were examined for interference with the interaction between FGFR2 or FGFR3 and heparin. Heparin binding to the fragment crystalline fusion of the extracellular domain of FGFR3 (FGFR3/Fc) or FGFR2 (FGFR2/Fc) was measured in the presence of PRO-007, PRO-001 and PRO-008 antibodies. Heparin Sepharose anchored FGFR3/Fc or FGFR2/Fc were incubated with the indicated antibodies. Bound (B) and unbound (U) fractions were then analyzed using Coomassie-stained SDS-PAGE. As shown in FIG. 12, FGFR3 was located entirely in the unbound fraction in the presence of either PRO-001 or PRO-007. The scFv and the Fab format of both antibodies demonstrated equal receptor dissociating activity. In contrast, FGFR3 remained heparin bound in the presence of PRO-008 Fab. These results demonstrate that contrary to PRO-001 and PRO-007 which compete with heparin, PRO-008 does not bind the receptor in the heparin binding domain. FIG. 12 further demonstrates that PRO-007 also competes with heparin binding to FGFR2.

Example 10

Inhibition of ERK Phosphorylation by PRO-007 in RCJ Cells

RCJ Cell Assay

Figure 13:
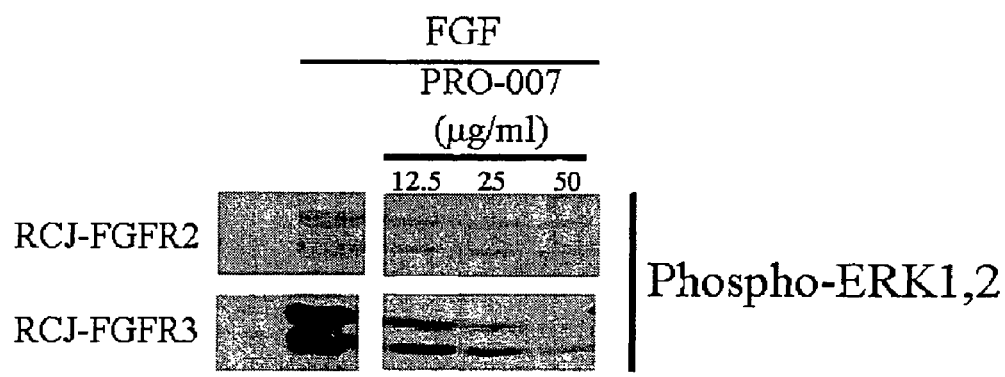
FIG. 13. PRO-007 induces dose dependent inhibition of ERK phosphorylation in RCJ cells specifically expressing FGFR2 or FGFR3.

RCJ cells (fetal rat calvaria-derived mesenchymal cells, RCJ 3.1C5.18; Grigoriadis, 1988) were generated to express various FGF receptors in an inducible manner, in the absence of tetracycline. RCJ cells that stably express either FGFR1, FGFR2 or FGFR3 were stimulated for 5 minutes with 20 ng/ml of either FGF2 (stimulating FGFR1 and FGFR2, ProChon Biotech Ltd., Rehovot, Israel) or FGF9 (stimulating FGFR3, ProChon Biotech Ltd., Rehovot, Israel). Parallel cultures were pre-incubated for 20 minutes with either 12.5 µg/ml, 25 µg/ml or 50 µg/ml of PRO-007. Cell lysates were analyzed by Western blot with anti-phospho-ERK (Sigma) followed by HRP-secondary antibody. ECL-exposed X-ray demonstrates that increasing amounts of PRO-007 inhibit ligand-dependent receptor phosphorylation in RCJ cells specifically expressing FGFR2 or FGFR3 (FIG. 13).

Example 11

Examining PRO-007 in Additional Bladder Cancer Cell Lines

In addition to RT112, SW780, 5637, RT4 and Jon TCC cell lines MGHU3 and 97-7 bladder cancer cell lines are also examined for the effect of PRO-007. MGHU3 and the 97-7 cells are seeded at a concentration of about 2000 cells/well in a 96 well plate. The next day, PRO-007sc or a control scFv are added at increasing concentrations. Five days latter, cell proliferation is measured by XTT.

Example 12

Examining PRO-007 in Bladder Cancer Cells from Human Patients

The aim in this study is to test the effects of neutralizing anti-FGFR antibodies on primary cultures of human bladder cancer and to compare them to normal bladder cells.

Patients

Five to ten patients undergoing transurethral resection of bladder tumor (TUR-BT) form the experimental group and 5-10 patients undergoing open transvesical prostatectomy for benign prostate hyperplasia (BPH) serve as controls. Pathological characteristic of the tumors is obtained from histopathological analysis.

Methods

A small part of the resected tumor (<1% of the tumor) or normal bladder is removed for establishment of a primary cell culture. Samples are transported in sterile Hanks' balanced salt solution (HBSS) containing 10 mM Hepes and 20 KIU/ml of aprotonin. Samples are washed in transport medium to remove excess blood cells, and incubated at 4° C. in 0.02% EDTA in phosphate-buffered saline (PBS) overnight; EDTA is replaced at least once during incubation. The following morning the urothelium is gently removed using fine forceps or a scalpel blade. Urothelial sheets are washed twice in HBSS and digested to a single-cell suspension with 200 U/ml of collagenase type IV for 10 min at 37° C. Cells are washed in keratinocyte serum-free medium containing 30 ng/ml cholera toxin and 100 µg/ml of penicillin/streptomycin solution (KSFM). Cells are resuspended in fresh KSFM and placed in 25 cm2 culture flasks at a density of 4×104/cm2 and incubated at 37° C. in 5% CO2.

Cells are passaged by incubating with 0.02% EDTA at 37° C. for 10 min, followed by trypsin-EDTA (Sigma) for a further 60 s. Cells are disaggregated by gentle agitation, and then serum containing medium is added to the flask to neutralize residual trypsin.

Analysis of FGFR Expression

All samples are analyzed for FGFRs expression using Western blotting. On the first splitting, part of the cells are grown for whole cell protein extraction and processed for immunoblotting using anti-FGFRs antibodies.

Viability Assay

Cell viability is assessed by XTT dye absorbance. Cells are seeded in 96-well plates at a density of 3,000-10,000 cells per well in culture medium. Cells are incubated in the absence or presence of increasing concentrations of the PRO-007 antibody. Plates are incubated for 48 or 72 hours at 37° C., 5% CO2. XTT assays are performed according to the manufacturer's instruction.

Data Analysis

The results of cell viability from tumor and normal cells are correlated with FGFR expression levels, grade and pathological stage of the disease.

While certain embodiments of the invention have been illustrated and described, it will be clear that the invention is not limited to the embodiments described herein. Numerous modifications, changes, variations, substitutions and equivalents will be apparent to those skilled in the art without depart-

REFERENCES

Bange J, Prechtl D, Cheburkin Y, Specht K, Harbeck N, Schmitt M, Knyazeva T, Muller S, Gartner S, Sures I, Wang H, Imyanitov E, Haring H U, Knayzev P, Iacobelli S, Hofler H, Ullrich A. Cancer progression and tumor cell motility are associated with the FGFR4 Arg(388) allele. Cancer Res. 62(3):840-7. 2002.

Bernard-Pierrot I, Ricol D, Cassidy A, Graham A, Elvin P, Caillault A, Lair S, Broet P, Thiery J P, Radvanyi F. Inhibition of human bladder tumour cell growth by fibroblast growth factor receptor 2b is independent of its kinase activity. Involvement of the carboxy-terminal region of the receptor. Oncogene. 23(57):9201-11. 2004.

Better M, Chang C P, Robinson R R, Horwitz A H. *Escherichia coli* secretion of an active chimeric antibody fragment. Science. 240(4855):1041-3. 1988.

Billerey C, Chopin D, Aubriot-Lorton M H, Ricol D, Gil Diez de Medina S, Van Rhijn B, Bralet M P, Lefrere-Belda M A, Lahaye J B, Abbou C C, Bonaventure J, Zafrani E S, van der Kwast T, Thiery J P, Radvanyi F. Frequent FGFR3 mutations in papillary non-invasive bladder (pTa) tumors. Am J. Pathol. 158(6):1955-9. 2001.

Cabilly S, Riggs A D, Pande H, Shively J E, Holmes W E, Rey M, Perry L J, Wetzel R, Heyneker H L. Generation of antibody activity from immunoglobulin polypeptide chains produced in *Escherichia coli*. Proc Natl Acad Sci USA. 81(11):3273-7. 1984.

Cappellen D, De Oliveira C, Ricol D, de Medina S, Bourdin J, Sastre-Garau X, Chopin D, Thiery J P, Radvanyi F. Frequent activating mutations of FGFR3 in human bladder and cervix carcinomas. Nat. Genet. 23(1):18-20. 1999.

Colligan et al (Eds.), Current Protocols in Immunology, Chapter 17, Section 17.1. 1992-2000, Easton D F et al. Genome-wide association study identifies novel breast cancer susceptibility loci. Nature. 2007.

Ezzat S, Zheng L, Zhu X F, Wu G E, Asa S L. Targeted expression of a human pituitary tumor-derived isoform of FGF receptor-4 recapitulates pituitary tumorigenesis. Clin Invest. 109(1):15-6. 2002.

Fortin D, Rom E, Sun H, Yayon A, Bansal R. Distinct fibroblast growth factor (FGF)/FGF receptor signaling pairs initiate diverse cellular responses in the oligodendrocyte lineage. J. Neurosci. 25(32):7470-9. 2005.

Goodman and Gilman's: The Pharmacological Bases of Therapeutics, 8th ed., Pergamon Press, 1990.

Hunter D J et al. A genome-wide association study identifies alleles in FGFR2 associated with risk of sporadic postmenopausal breast cancer. Nat. Genet. 2007.

Ishiwata T, Friess H, Buchler M W, Lopez M E, Korc M. Characterization of keratinocyte growth factor and receptor expression in human pancreatic cancer. Am J. Pathol. 153(1):213-22. 1998.

Johnston C L, Cox H C, Gomm J J, Coombes R C Fibroblast growth factor receptors (FGFRs) localize in different cellular compartments. A splice variant of FGFR-3 localizes to the nucleus J Biol. Chem. 270(51):30643-50. 1995.

Kan M, Wang F, Xu J, Crabb J W, Hou J, McKeehan W L. An essential heparin-binding domain in the fibroblast growth factor receptor kinase. Science. 259(5103):1918-21. 1993.

Khnykin D, Troen G, Berner J M, Delabie J. The expression of fibroblast growth factors and their receptors in Hodgkin's lymphoma. J. Pathol. 208(3):431-8. 2006.

Knappik A, Ge L, Honegger A, Pack P, Fischer M, Wellnhofer G, Hoess A, Wolle J, Pluckthun A, Vimekas B. Fully synthetic human combinatorial antibody libraries (HuCAL) based on modular consensus frameworks and CDRs randomized with trinucleotides. J Mol. Biol. 296(1):57-86. 2000.

Kohler G, Baumann B, Iglesias A, McCubrey J, Potash M J, Traunecker A, Zhu D. Different ways to modify monoclonal antibodies. Med Oncol Tumor Pharmacother. 1(4): 227-33. 1984.

Kurban G, Ishiwata T, Kudo M, Yokoyama M, Sugisaki Y, Naito Z. Expression of keratinocyte growth factor receptor (KGFR/FGFR2IIIb) in human uterine cervical cancer. Oncol Rep. 11(5):987-91. 2004.

Lorenzi M V, Horii Y, Yamanaka R, Sakaguchi K, Miki T FRAG1, a gene that potently activates fibroblast growth factor receptor by C-terminal fusion through chromosomal rearrangement. Proc Natl Acad Sci USA. 93(17):8956-61. 1996.

Martínez-Torrecuadrada J, Cifuentes J, López-Serra P, Saenz, P, Martinez A and Casal J I. Targeting the Extracellular Domain of Fibroblast Growth Factor Receptor 3 with Human Single-Chain Fv Antibodies Inhibits Bladder Carcinoma Cell Line Proliferation. Clinical Cancer Research 11: 6280-6290.2005.

Meinkoth J, Wahl G. Hybridization of nucleic acids immobilized on solid supports. Anal Biochem. 138(2):267-84. 1984.

Müller K M, Arndt K M, Strittmatter W, Plückthun A. The first constant domain (C(H)1 and C(L)) of an antibody used as heterodimerization domain for bispecific miniantibodies. FEBS Lett. 422(2):259-64. 1998.

Ornitz D M, Itoh N. Fibroblast growth factors. Genome Biol. 2(3) reviews 3005. 1-reviews 3005.12. 2001.

Remington's Pharmaceutical Sciences, 17th ed., Mack Publishing Co., Easton, Pa., 1990.

Ricol D, Cappellen D, El Marjou A, Gil-Diez-de-Medina S, Girault J M, Yoshida T, Ferry G, Tucker G, Poupon M F, Chopin D, Thiery J P, Radvanyi F. Tumour suppressive properties of fibroblast growth factor receptor 2-IIIb in human bladder cancer. Oncogene.18(51):7234-43. 1999.

Saltzman W M, Langer R. Transport rates of proteins in porous materials with known microgeometry. Biophys J. 55(1):163-71. 1989.

Sambrook et al., Molecular Cloning: A Laboratory Manual, 2d edition, Cold Spring Harbor Press. 1989.

Sherwood J K, Dause R B, Saltzman W M. Controlled antibody delivery systems. Biotechnology (NY). 10(11):1446-9. 1992.

van Rhijn B W, van Tilborg A A, Lurkin I, Bonaventure J, de Vries A, Thiery J P, van der Kwast T H, Zwarthoff E C, Radvanyi F. Novel fibroblast growth factor receptor 3 (FGFR3) mutations in bladder cancer previously identified in non-lethal skeletal disorders. Eur J Hum Genet. 10(12): 819-24. 2002.

Yee C J, Lin O, Boyd J. Analysis of fibroblast growth factor receptor 3 S249C mutation in cervical carcinoma. J Natl Cancer Inst. 92(22):1848-9. 2000.

Zhang B, Xu G, Evans J S. Model peptide studies of sequence repeats derived from the intracrystalline biomineralization protein, SM50. II. Pro, Asn-rich tandem repeats. Biopolymers. 54(6):464-75. 2000.

Zieger K, Dyrskjot L, Wiuf C, Jensen J L, Andersen C L, Jensen K M, Orntoft T F. Role of activating fibroblast growth factor receptor 3 mutations in the development of bladder tumors. Clin Cancer Res. 11(21):7709-19. 2005.

The invention claimed is:

1. A molecule comprising at least the antigen-binding portion of an antibody which has affinity for fibroblast growth factor receptor 2 (FGFR2), with cross-reactivity to fibroblast growth factor receptor 3 (FGFR3), which blocks both ligand-dependent and constitutive ligand-independent receptor activation.

2. The molecule according to claim 1 wherein the antibody binds both FGFR2 and FGFR3 with affinity of at least 50 nM but is substantially devoid of affinity to fibroblast growth factor receptor 1 (FGFR1).

3. The molecule according to claim 1 wherein the antibody is selected from a monoclonal antibody having binding affinity to FGFR2 with cross-reactivity to FGFR3, a proteolytic fragment of said monoclonal antibody and a single chain antibody, wherein said fragment of an antibody is a single chain Fv having an amino acid sequence set forth in SEQ ID NO:5.

4. The molecule according to claim 3 wherein the antibody or antibody fragment is modified by PEGylation.

5. A pharmaceutical composition comprising at least one molecule comprising at least the antigen-binding portion of an antibody which has affinity for fibroblast growth factor receptor 2 (FGFR2) with cross-reactivity to fibroblast growth factor receptor 3 (FGFR3), which blocks both ligand-dependent and constitutive ligand-independent receptor activation; and a pharmaceutically acceptable carrier.

6. The pharmaceutical composition according to claim 5 wherein the molecule binds both FGFR2 and FGFR3 with affinity of at least 50 nM but is substantially devoid of affinity to fibroblast growth factor receptor 1 (FGFR1).

7. The pharmaceutical composition according to claim 5 wherein the molecule is selected from a monoclonal antibody having binding affinity to FGFR2 with cross-reactivity to FGFR3, a proteolytic fragment of said monoclonal antibody and a single chain antibody, wherein said fragment of an antibody is a single chain Fv having an amino acid sequence set forth in SEQ ID NO:5.

8. The pharmaceutical composition according to claim 7 wherein the antibody or antibody fragment is modified by PEGylation.

9. A molecule comprising at least the antigen-binding portion of an antibody which has affinity for fibroblast growth factor receptor 2 (FGFR2) with cross-reactivity to fibroblast growth factor receptor 3 (FGFR3), which blocks both ligand-dependent and constitutive ligand-independent receptor activation, wherein the antigen-binding portion comprises a single chain Fv having an amino acid sequence set forth in SEQ ID NO:5.

10. The molecule according to claim 9 wherein the antibody is modified by PEGylation.

11. A pharmaceutical composition comprising at least one molecule according to claim 9; and a pharmaceutically acceptable carrier.

12. A method for attenuating or treating bladder cancer associated with fibroblast growth factor receptor 2 (FGFR2), comprising administering to an individual in need thereof a therapeutically effective amount of the molecule according to claim 1; and a pharmaceutically acceptable carrier.

13. The method according to claim 12 wherein said molecule is selected from a monoclonal antibody, a proteolytic fragment of a monoclonal antibody and a single chain antibody, wherein said fragment of an antibody is a single chain Fv having an amino acid sequence set forth in SEQ ID NO:5.

14. The method according to claim 13 wherein said antibody or antibody fragment is modified by PEGylation.

15. A method for attenuating or treating bladder cancer associated with fibroblast growth factor receptor 2(FGFR2), comprising administering to an individual in need thereof a therapeutically effective amount of the molecule according to claim 9; and a pharmaceutically acceptable carrier.

16. A method for attenuating or treating bladder cancer associated with fibroblast growth factor receptor 2 (FGFR2), comprising administering to an individual in need thereof a therapeutically effective amount of the pharmaceutical composition according to claim 11.

* * * * *